US007045291B2

(12) United States Patent
Hanson et al.

(10) Patent No.: US 7,045,291 B2
(45) Date of Patent: May 16, 2006

(54) MULTIPLEX PCR FOR THE DETECTION OF AMPC BETA-LACTAMASE GENES

(75) Inventors: Nancy Jo Dohse Hanson, Gretna, NE (US); Francisco-Javier Perez Perez, Vitoria (ES)

(73) Assignee: Creighton University, Omaha, NE (US)

( * ) Notice: Subject to any disclaimer, the term of this patent is extended or adjusted under 35 U.S.C. 154(b) by 407 days.

(21) Appl. No.: 10/147,601

(22) Filed: May 17, 2002

(65) Prior Publication Data
US 2003/0219749 A1 Nov. 27, 2003

(51) Int. Cl.
C12Q 1/68 (2006.01)
C12P 10/34 (2006.01)
C07H 21/04 (2006.01)

(52) U.S. Cl. .................. 435/6; 435/91.2; 536/24.33
(58) Field of Classification Search ............... 435/6, 435/91.2; 426/23.33; 536/24.33
See application file for complete search history.

(56) References Cited

U.S. PATENT DOCUMENTS

| 4,683,194 A | 7/1987 | Saiki et al. |
| 4,683,195 A | 7/1987 | Mullis et al. |
| 5,840,549 A * | 11/1998 | First et al. ................ 435/91.2 |
| 5,994,066 A | 11/1999 | Bergeron et al. |
| 6,001,564 A | 12/1999 | Bergeron et al. |
| 6,210,885 B1 | 4/2001 | Gjerde et al. |
| 6,238,868 B1 | 5/2001 | Carrino et al. |
| 6,242,223 B1 * | 6/2001 | Hanson et al. ............ 435/91.2 |
| 6,303,288 B1 | 10/2001 | Furcht et al. |
| 6,309,833 B1 | 10/2001 | Edman et al. |
| 6,379,889 B1 * | 4/2002 | Apffel et al. ................ 435/6 |

FOREIGN PATENT DOCUMENTS

| WO | WO 91/08305 | 6/1991 |
| WO | WO 2001/23604 A2 | 4/2001 |
| WO | WO 2001/23604 A3 | 4/2001 |
| WO | WO 02/086153 A1 | 10/2002 |

OTHER PUBLICATIONS

"Designer PCR™" from Research Genetics (2130 Memorial Parkway SW, Huntsville, AL). Advertisement in *Nucleic Acis Res.*, 22(15) 1994.
Barnaud et al., "Extension of Resistance to Cefepime and Cefpirome Associated to a Six Amino Acid Deletion in the H-10 Helix of the Cephalosporinase of an *Enterobacter Cloacae* Clinical Isolate," *FEMS Microbiology Letters*, 195(2):185-190 (2001).
Galleni et al., "Sequence and comparative analysis of three *Enterobacter cloacae ampC* β-lactamase genes and their products," *Biochem. J.*, 250, 753-760 (1988).
Gonzalez Leiza et al., "Gene sequence and biochemical characterization of FOX-1 from *Klebsiella pneumoniae*, a newe AmpC-type plasmid-mediated beta-lactamase with two molecular variants," *Antimicrob. Agents Chemother.*, 38(9):2150-7 (1994).
Huletsky et al., "Nucleotide Sequence and Phylogeny of SHV-2 β-Lactamase," *Antimicrob. Agents Chemother.*, 34(9):1725-1732 (1990).
Leung et al., "Rarity of transferable β-lactamase production by *Klebsiella* species," *J. Antimicrob. Chemother.*, 39:737-745 (1997).
Martineau et al., "Species-specific and ubiquitous DNA-based assays for rapid identification of *Staphylococcus epidermidis*," *J. Clin. Microbiol.*, 34(12):2888-93 (1996).
National Center for Biotechnology Information, National Library of Medicine, National Institutes of Health, Bethesda, MD. GenBank accession No. AY034848: *Klebsiella pneumoniae* : <http://www.ncbi.nlm.nih.gov/entrez/query.fcgi?cmd=Retrieve&db=nucleotide&list_uids=14626421&dopt=GenBank> (retrieved on Sep. 27, 2002).
Transgenomic |Products and Technology; "Nucleic Acid Separations—WAVE® Nucleic Acid Fragment Analysis System Technology—Instruments & Accessories" <http://www.transgenomic.com/Pages/ProductWave.html> (retrieved on Nov. 8, 2001).
Transgenomic |Products and Technology; "WAVE® System Technologies" <http://www.transgenomic.com/Pages/ProductWave.html> (retrieved on Feb. 22, 2002).
Acar et al., "Nature of the Resistance Problem," *Clin. Inf. Dis.*, 24 (Suppl 1):S1 (1997).
Arlet et al., "Construction by polymerase chain reaction and intragenic DNA probes for three main types of transferable β-lactamases (TEM, SHV, CARB)," *FEMS Microbiol. Lett.*, 82:19-25 (1991).
Arlet et al., "Molecular characterization by PCR-restriction fragment length polymorphism of TEM β-lactamases," *FEMS Microbiol. Lett.*, 134:203-208 (1995).
Arlet et al., "Substitution of alanine for aspartate at position 179 in the SHV-6 extended-spectrum β-lactamases," *FEMS Microbiol. Lett.*, 152:163-167 (1997).
Barnaud et al., "Cloning and sequencing of the gene encoding the AmpC β-lactamase of *Morganella morganii*," *FEMS Microbiol. Lett*, 148:15-20 (1997).

(Continued)

*Primary Examiner*—Kenneth R. Horlick
*Assistant Examiner*—Joyce Tung
(74) *Attorney, Agent, or Firm*—Mueting, Raasch & Gebhardt, P.A.

(57) ABSTRACT

Oliognucleotide primers are provided that are specific for nucleic acid characteristic of certain AmpC beta-lactamases. The primers can be employed in methods to detect the presence or absence of an AmpC beta-lactamase gene in samples, and to identify nucleic acid characteristic of AmpC beta-lactamase genes in samples, particularly, in clinical isolates of Gram-negative bacteria.

25 Claims, 7 Drawing Sheets

OTHER PUBLICATIONS

Bauernfeind et al., "A New Plasmidic Cefotaximase in a Clinical Isolate of *Escherichia coli*," *Infection*, 18(5):294-298 (1990).

Billot-Klein et al., "Nucleotide Sequence of the SHV-5 β-Lactamase Gene of a *Klebsiella pneumoniae* Plasmid," *Antimicrob. Agents Chemother.*, 34(12):2439-2441 (1990).

Birnboim et al., "A rapid alkaline extraction procedure for screening recombinant plasmid DNA," *Nucleic Acids Res.*, 7(6):1513-1523 (1979).

Bradford et al., "SHV-7, a Novel Cefotaxime-Hydrolyzing β-Lactamase, Identified in *Escherichia coli* Isolates from Hospitalized Nursing Home Patients," *Antimicrob. Agents Chemother.*, 39(4):899-905 (1995).

Bradford et al., "Multiply Resistant *Klebsiella pneumoniae* Strains from Two Chicago Hospitals: Identification of the Extended-Spectrum TEM-12 and TEM-10 Ceftazidime-Hydrolyzing β-Lactamases in a Single Isolate," *Antimicrob. Agents Chemother.*, 38(4): 761-766 (1994).

Bret et al., "Chromosomally Encoded AmpC-Type β-Lactamase in a Clinical Isolate of *Proteus mirabilis*," *Antimicrob. Agents Chemother.*, 42(5):1110-1114 (1998).

Brun-Buisson et al., "Transferable Enzymatic Resistance to Third-Generation Cephalosporins During Nosocomial Outbreak of Multiresistant *Klebsiella Pneumoniae*," *The Lancet*, 2:302-306 (1987).

Burns et al., "An Integrated Nanoliter DNA Analysis Device," *Science*, 282:484-487 (1998).

Caniça et al., "Molecular Diversity and Evolution of $bla_{tem}$ Genes Encoding β-Lactamases Resistant to Clavulanic Acid in Clinical *E. coli*," *J. Mol. Evol.*, 44:57-65 (1997).

Carter et al., "Use of a non-radioactive hybridisation assay for direct detection of gram-negative bacteria carrying TEM β-lactamase genes in infected urine," *J. Med. Microbiol*, 28:113-117 (1989).

Check, "Clinical Microbiology Eyes Nucleic Acid-Based Technologies," *ASM News*, 64(2):84-89 (1998).

Crea et al., "Chemical synthesis of genes for human insulin," *Proc. Natl. Acad. Sci. USA*, 75(12):5765-5769 (1978).

Crosa et al., "Plasmids," *Manual of Methods for General Bacteriology*, Gerhardt et al., eds., American Society for Microbiology, Washington, DC, Ch.15, pp. 266-282 (1981).

Curran et al., "A rapid immunoassay method for the direct detection of PCR products: application to detection of TEM β-lactamase genes," *J. Med. Microbiol.*, 45:76-78 (1996).

Gold et al., "Antimicrobial-Drug Resistance," *The New England Journal of Medicine*, 335(19):1445-1453 (1996).

Hanson et al., "Molecular Characterization of a Multiply Resistant *Klebsiella pneumoniae*," Abstract C-59, 37th *ICAAC*, Toronto, Ontario, Canada, Sep. 28-Oct. 1, (1997).

Hanson et al., "A Novel TEM-Type Extended Spectrum Beta-Lactamase Expressed in Three Different Genera of Enterobacteriaceae from South Africa," Abstract C-5, p. 70, 38th *ICAAC*, San Diego, California, Sep. 24-27 (1998).

Hanson et al., "Molecular characterization of a multiply resistant *Klebsiella pnuemoniae* encoding ESBLs and a plasmid-mediated AmpC," *J. Antimicrob. Chemother.*, 44:377-380 (1999).

Hanson et al., "Regulation of Inducible AmpC Beta-Lactamase Expression Among *Enterobacteriaceae*," *Curr. Pharmac. Design*, 5(11):881-894 (1999).

Hibbert-Rogers et al., "Convergent evolution of TEM-26, a β-lactamase with extended-spectrum activity," *J. Antimicrob. Chemother.*, 33:707-720 (1994).

Jacoby et al., "More Extended-Spectrum β-Lactamases," *Antimicrob. Agents Chemother.*, 35(9):1697-1704 (1991).

Jarlier et al., "Extended Broad-Spectrum β-Lactamases Conferring Transferable Resistance to Newer β-Lactam Agents in *Enterobacteriaceae*: Hospital Prevalence and Susceptibility Patterns," *Rev. Infect. Dis.*, 10(4):867-878 (1988).

Jones, "The Emergent Needs for Basic Research, Education, and Surveillance of Antimicrobial Resistance: Problems Facing the Report from the American Society for Microbiology Task Force on Antibiotic Resistance," *Diagn. Microbiol. Infect. Disease*, 25:153-161 (1996).

Jones, "Important and Emerging β-Lactamase-mediated Resistances in Hospital-based Pathogens: The Amp C Enzymes," *Diagn. Microbiol. Infect. Dis.*, 31:461-466 (1998).

Leegaard et al., "Antibiotic resistance mechanisms in *Salmonella* species causing bacteraemia in Malawi and Kenya", *APMIS*, 104:302-306 (1996).

M'Zali et al., "Brief reports: Detection of mutations conferring extended-spectrum activity of SHV β-lactamases using polymerase chain reaction single strand conformational polymorphism (PCR-SSCP)," *J. Antimicrob. Chemother.*, 37:797-802 (1996).

Mabilat et al., "Direct Sequencing of the Amplified Structural Gene and Promoter for the Extended-Broad-Spectrum β-Lactamase TEM-9 (RHH-1) of *Klebsiella pneumoniae*," *Plasmid*, 23:27-34 (1990).

Mabilat et al., "Development of "Oligotyping" for Characterization and Molecular Epidemiology of TEM β-Lactamases in Members of the Family *Enterobacteriaceae*," *Antimicrob. Agents Chemother.*, 34(11):2210-2216 (1990).

Maniatis et al., *Molecular Cloning: A Laboratory Manual*, Cold Spring Harbor, NY (Title page, Publication page, and Table of Contents only) 8 pgs. (1982).

Marchese et al., "Characterization of FOX-3, an AmpC-Type Plasmid-Mediated β-Lactamase from an Italian Isolate of *Klebsiella oxytoca*," *Antimicrob. Agents Chemother.*, 42(2):464-467 (1998).

Medeiros, "Recent Increases in Resistance: Mechanisms and Organisms: Evolution and Dissemination of β-Lactamases Accelerated by Generations of β-Lactam Antibiotics," *Clin. Inf. Dis.*, 24(Suppl 1):S19-45 (1997).

Mugnier et al., "A TEM-Derived Extended-Spectrum β-Lactamase in *Pseudomonas aeruginosa*," *Antimicrob. Agents Chemother.*, 40(11):2488-2493 (1996).

Mullis et al., "Specific Enzymatic Amplification of DNA In Vitro: The Polymerase Chain Reaction," *Cold Spring Harbor Symposia on Quantitative Biology*, Cold Spring Harbor Laboratory, Cold Spring Harbor, NY, 51:263-273 (1986).

Mullis et al., "Specific Enzymatic Amplification of DNA *In Vitro:* The Polymerase Chain Reaction," *Milestones in Biotechnology: Classic Papers on Genetic Engineering*, Davies et al., eds., Buterworth-Heinemann, Stoneham, MA, pp. 17-27 (1992).

Naumovski et al., "Outbreak of Ceftazidime Resistance Due to a Novel Extended-Spectrum β-Lactamase in Isolates from Cancer Patients," *Antimicrob. Agents Chemother.*, 36(9):1991-1996 (1992).

Nordmann et al., "Characterization of a Novel Extended-Spectrum β-Lactamase from *Pseudomonas aeruginosa*," *Antimicrob. Agents Chemother.*, 37(5): 962-969 (1993).

Nüesch-Inderbinen et al., "Detection of Genes Coding for Extended-Spectrum SHV Beta-Lactamases in Clinical Isolates by a Molecular Genetic Method, and Comparison with the E Test," *Eur. J. Clin. Microbiol. Infect. Dis., 15:*398-402 (1996).

O'Callaghan et al., "Inhibition of β-Lactamase Decomposition of Cephaloridine and Cephalothin by Other Cephalosporins," *Antimicrob. Agents Chemother.,* 337-343 (1967).

Perez et al., "The Use of Multiplex PCR for the Detection of Plasmid-Mediated AmpC β-lactamase Genes in Clinical Isolates," *Department of Medical Microbiology and Immunology—Center for Research in Anti-Infectives and Biotechnology—Creighton University School of Medicine* (Nov. 2001): (published in *Journal of Clinical Microbiology* Jun. 2002).

Philippon et al., "Minireview—Extended-Spectrum β-Lactamases," *Antimicrob. Agents Chemother., 33*(8):1131-1136 (1989).

Piddock et al., "Prevalence and mechanism of resistance to 'third-generation' cephalosporins in clinically relevant isolates of Enterobacteriaceae from 43 hospitals in the UK, 1990-1991," *J. Antimicrob.Chemother., 39:*177-187 (1997).

Pitout et al., "β-Lactamases Responsible for Resistance to Expanded-Spectrum Cephalosporins among *Klebsiella pneumoniae, Escherichia coli* and *Proteus mirabilis* Isolates Recovered in South Africa," *96th ASM General Meeting,* Poster and Abstract A-46, p. 141 (May 1996).

Pitout et al., "Plasmid-Mediated Resistance to Expanded-Spectrum Cephalosporins among *Enterobacter aerogenes* Strains," *Antimicrob. Agents Chemother., 42*(3):596-600 (1998).

Prodinger et al., "Molecular Epidemiology of *Klebsiella pneumoniae* Producing SHV-5 62 -Lactamase: Parallel Outbreaks Due to Multiple Plasmid Transfer," *J. Clin. Microbio., 34*(3):564-568 (1996).

Roth et al., "Nucleic Acid Biotechnology," *Annu. Rev. Biomed. Eng., 01:*265-297 (1999).

Saiki et al., "Enzymatic Amplification of β-Globin Genomic Sequences and Restriction Site Analysis for Diagnosis of Sickle Cell Anemia," *Science, 230,* 1350-1354 (1985).

Saiki et al., "Analysis of enzymatically amplified β-globin and HLA-DQα DNA with allele-specific oligonucleotide probes," *Nature,* 324:163-166 (1986).

Sanchez et al., "The E-Test Applied to Susceptibility Tests of Gonococci, Multiply-Resistant Enterococci, and Enterobacteriaceae Producing Potent β-Lactamases," *Diagn. Microbiol. Infect. Dis., 15:*459-463 (1992).

Sanders et al., "New Service Notification," distributed by Center for Research in Anti-Infectives and Biotechnology, Creighton University School of Medicine (Sep. 28, 1997).

Sanders et al., "Characterization of β-Lactamases In Situ on Polyacrylamide Gels," *Antimicrob. Agents Chemother., 30*(6):951-952 (1986).

Sanders, Jr. et al., "*Enterobacter* spp.: Pathogens Poised To Flourish at the Turn of the Century," *Clin. Microbiol. Rev., 10*(2):220-241 (1997).

Sanders et al., "Ability of the VITEK 2 Advanced Expert System to Identify β-Lactam Phenotypes in Isolates of Enterobacteriaceae and *Pseudomonas aeruginosa,*" *Journal of Clinical Microbiology, 38*(2):570-574 (2000).

Sayeed et al., "Expression of *Aeromonas caviae bla* genes in *Escherichia coli,*" *J. Antimicrob. Chemother., 38:*435-441 (1996).

Scharf et al., "Direct Cloning and Sequence Analysis of Enzymatically Amplified Genomic Sequences," *Science, 233,* 1076-1078 (1986).

Schmitz et al., "Specific information concerning taxonomy, pathogenicity and methicillin resistance of staphylococci obtained by a multiplex PCR," *J. Med. Microbiol., 46:*773-778 (1997).

Sirot et al., "A Complex Mutant of TEM-1 β-Lactamase with Mutations Encountered in Both IRT-4 and Extended-Spectrum TEM-15, Produced by an *Escherichia coli* Clinical Isolate," *Antimicrob. Agents Chemother., 41*(6):1322-1325 (1997).

Siu et al., "Correlation of in vitro susceptibility testing results for amoxicillin-clavulanate and ampicillin-sulbactam using a panel of beta-lactamase-producing Enterobacteriaceae", *APMIS,* 106:917-920 (1998).

Speldooren et al., "Discriminatory detection of inhibitor-resistant beta-lactamases in *Escherichia coli* by single-strand conformation polymorphism-PCR", *Antimicrobial Agents and Chemotherapy, 42:*879-884 (1998).

Tenover et al., "Development of PCR Assays to Detect Ampicillin Resistance Genes in Cerebrospinal Fluid Samples Containing *Haemophilus influenzae,*" *J. Clin. Microb., 32*(11):2729-2737 (1994).

Tenover et al., "SHEA Position Paper: How to Select and Interpret Molecular Strain Typing Methods for Epidemiological Studies of Bacterial Infections: A Review for Healthcare Epidemiologists," *Infect. Control and Hosp. Epidemiol., 18*(6):426-439 (1997).

Thomson et al., "High-Level Resistance to Cefotaxime and Ceftazidime in *Klebsiella pneumoniae* Isolates from Cleveland, Ohio," *Antimicrob. Agents Chemother., 35*(5):1001-1003 (1991).

Thomson et al., "Detection of Extended-Spectrum β-Lactamases in Members of the Family *Enterobacteriaceae:* Comparison of the Double-Disk and Three-Dimensional Tests," *Antimicrob. Agents Chemother., 36*(9):1877-1882 (1992).

Tolmansky, "Sequencing and Expression of *aadA, bla, and tnpR* from the Multiresistance Transposon Tn*1331,*" *Plasmid, 24,* 218-226 (1990).

Towner, "Leading article: Detection of antibiotic resistance genes with DNA probes," *J. Antimicrob. Chemother., 30:*1-2 (1992).

Vahaboglu et al., "Pratical approach for detection and identification of OXA-10-derived ceftazidime-hydrolyzing extended spectrum beta-lactamases", *J. Clin. Microbiology, 36:*827-829 (1998).

Vercauteren et al., "Comparison of Screening Methods for Detection of Extended-Spectrum β-Lactamases and Their Prevalence among Blood Isolates of *Escherichia coli* and *Klebsiella* spp. in a Belgian Teaching Hospital," *J. Clin. Microb., 35*(9):2191-2197 (1997).

Walsh et al., "Sequence analysis of two chromosomally mediated inducible β-lactamases from *Aeromonas sobria,* strain 163a, one a class D penicillinase, the other an AmpC cephalosporinase," *J. Antimicrob. Chemother., 36:* 41-52 (1995).

Zhou et al., "Emergence of Clinical Isolates of *Escherichia coli* Producing TEM-1 Derivatives or an OXA-1 β-Lactamase Conferring Resistance to β-Lactamase Inhibitors," *Antimicrob. Agents Chemother., 38*(5):1085-1089 (1994).

\* cited by examiner

MULTIPLEX PCR FOR THE DETECTION OF AMPC BETA-LACTAMASE GENES

BACKGROUND

A disturbing consequence of the use, and over-use, of beta-lactam antibiotics (e.g., penicillins and cephalosporins) has been the development and spread of beta-lactamases. Beta-lactamases are enzymes that open the beta-lactam ring of penicillins, cephalosporins, and related compounds, to inactivate the antibiotic. The production of beta-lactamases is an important mechanism of resistance to beta-lactam antibiotics among Gram-negative bacteria.

Expanded-spectrum cephalosporins have been specifically designed to resist degradation by the older broad-spectrum beta-lactamases such as TEM-1, 2, and SHV-1. Microbial response to the expanded-spectrum cephalosporins has been the production of mutant forms of the older beta-lactamases called extended-spectrum beta-lactamases (ESBLs). Although ESBL-producing Enterobacteriaceae were first reported in Europe in 1983 and 1984, ESBLs have now been found in organisms of diverse genera recovered from patients in all continents except Antarctica. The occurrence of ESBL-producing organisms varies widely with some types more prevalent in Europe (TEM-3), others more prevalent in the United States (TEM-10, TEM-12 and TEM-26), while others appear worldwide (SHV-2 and SHV-5). These enzymes are capable of hydrolyzing the newer cephalosporins and aztreonam. Studies with biochemical and molecular techniques indicate that many ESBLs are derivatives of older TEM-1, TEM-2, or SHV-1 beta-lactamases, some differing from the parent enzyme by one to seven amino acid substitutions.

In addition, resistance in *Klebsiella pneumoniae* and *Escherichia coli* to cephamycins and inhibitor compounds such as clavalante have also arisen via acquisition of plasmids containing the chromosomally derived AmpC beta-lactamase, most commonly originating from *Enterobacter cloacae, Citrobacter freundii, Hafnia alvei,* and *Morganella morganii.*

It is of particular concern that genes encoding the beta-lactamases are often located on large plasmids that also contain genes for resistance to other antibiotic classes including aminoglycosides, tetracycline, sulfonamides, trimethoprim, and chloramphenicol. Furthermore there is an increasing tendency for bacteria to produce multiple beta-lactamases. These developments, which occur over a wide range of Gram-negative genera, represent a recent evolutionary development in which common Gram-negative bacteria are availing themselves of increasingly complex repertoires of antibiotic resistance mechanisms. Clinically, this increases the difficulty of identifying effective therapies for infected patients.

Organisms overexpressing AmpC beta-lactamases are a major clinical concern because these organisms are usually resistant to all the beta-lactam drugs except the dipolar ionic methoxyiminocephalosporins such as cefepime and cefpirome and the carbapenems. However, recently an *Enterobacter cloacae* clinical isolate associated high-level resistance to cefepime and cefpirome with overexpression of and a deletion within the ampC structural gene was reported. Barnaud et al., *FEMS Microbiology Letters,* 195:185–190 (2001).

Overexpression of AmpC beta-lactamases can occur in two ways, the deregulation of the chromosomal gene expressing the AmpC beta-lactamase or the acquisition by gram-negative organisms of a transferable ampC gene either on a plasmid or other transferable element. The latter have commonly been called plasmid-mediated AmpC beta-lactamases.

The ability to identify the difference between constitutive overexpression of AmpC beta-lactamase from the chromosome or a plasmid is important for hospital epidemiology. Organisms with inducible chromosomal ampC beta-lactamase genes include *E. cloacae, E. aerogenes, Citrobacter freundii, Morganella morganii, Hafnia alvei, Serratia marcescens,* and indole positive *Proteus* spp. Strains of these organisms that overexpress the chromosomal genes are collectively called derepressed mutants. Therefore, by identifying the organism the laboratory can identify the ability of that organism to overexpress the AmpC beta-lactamase. *Escherichia coli* strains can also overexpress their chromosomal ampC beta-lactamase gene and are termed hyperproducing *E. coli.* Plasmid-mediated ampC genes are derived from the chromosomal ampC gene of several members of the family Enterobacteriaceae, such as *E. cloacae, C. freundii,* and others. But not all members of the family Enterobacteriaceae encode a gene for AmpC beta-lactamases or are the origin of plasmid-mediated genes, such as *K. pneumoniae* or *E. coli,* respectively. Therefore, the distinction between a plasmid-mediated AmpC beta-lactamase and the endogenous enzyme is difficult to determine in both hyper-producing *E. coli* strains and organisms with inducible chromosomal AmpC enzymes. This distinction, however, is critical for hospital infection control. Plasmid-mediated genes whether they are extended-spectrum beta-lactamases (ESBLs) or AmpC enzymes can spread rapidly to members of the same species or organisms of different genera. In addition, multiple beta-lactamases within one organism, such as multiple ESBLs or a combination of ESBLs and AmpC enzymes can make phenotypic identification of the AmpC enzyme difficult. Unfortunately, for these reasons, the detection of AmpC, particularly plasmid-mediated AmpC, beta-lactamase resistance goes undetected in most clinical laboratories.

The ability to distinguish between different types of ampC beta-lactamase nucleic acid in a clinical sample is useful for such epidemiological purposes as identifying how particular bacteria of interest have spread, thus aiding in infection control. It is also useful for identifying the proper antibiotic treatment for a patient. Thus, there is a need for techniques that can quickly and accurately identify the particular types of beta-lactamases that may be present in a clinical isolate or sample, for example. This could have significant implications in the choice of antibiotic necessary to treat a bacterial infection.

SUMMARY OF THE INVENTION

The present invention is directed to the use of oligonucleotide primers specific to nucleic acids characteristic of (typically, genes encoding) certain AmpC beta-lactamase genes. More specifically, the present invention uses primers to identify, preferably, ampC beta-lactamase nucleic acid (typically genes), more preferably, transferable ampC beta-lactamase nucleic acid, and even more preferably, plasmid-mediated ampC beta-lactamase nucleic acid, in samples, particularly in clinical isolates of Gram-negative bacteria. The method additionally provides a method for identifying the presence or absence of AmpC beta-lactamase gene in a clinical sample. Exemplary primers of the invention include the primer sequences set forth in SEQ ID NOs: 1–12. As used herein, a nucleic acid characteristic of an AmpC beta-lactamase gene includes a gene or a portion thereof. A "gene" as used herein is a segment or fragment of nucleic acid (e.g., a DNA molecule) involved in producing a peptide (e.g., a polypeptide and/or protein). A gene can include regions preceding (upstream) and following (downstream) a coding region (i.e., regulatory elements) as well as intervening sequences (introns, e.g., non-coding regions) between individual coding segments (exons). The term "coding region" is used broadly herein to mean a region capable of being transcribed to form an RNA. The transcribed RNA can be, but need not necessarily be, further processed to yield an mRNA.

A method for identifying the presence or absence of an AmpC beta-lactamase gene in a clinical sample is provided. Preferably, the clinical sample provided is characterized as a Gram-negative bacteria with resistance to beta-lactam antibiotics, and the ampC beta-lactamase nucleic acid are of a different origin relative to a bacteria's chromosomal ampC beta-lactamase nucleic acid. The method includes, providing a clinical sample; contacting the clinical sample with at least two pairs of oligonucleotide primers specific for nucleic acid of an AmpC beta-lactamase gene, wherein one primer of each pair is complementary to at least a portion of an ampC beta-lactamase nucleic acid in the sense strand and the other primer of each pair is complementary to at least a portion of an ampC beta-lactamase nucleic acid in the antisense strand; annealing the primers to the ampC beta-lactamase nucleic acid, if present; simultaneously extending the annealed primers from a 3' terminus of each primer to synthesize an extension product that is complementary to the nucleic acid strands annealed to each primer wherein each extension product after separation from the ampC beta-lactamase nucleic acid, if present, serves as a template for the synthesis of an extension product for the other primer of each pair; and analyzing the sample for the presence or absence of amplified products, wherein the presence of amplified products of a size characteristic of an ampC beta-lactamase nucleic acid indicates the presence of an AmpC beta-lactamase gene in the clinical sample. Analysis of the sample may include separating the amplified products from the sample and analyzing the separated amplified products for a size characteristic of a particular type of AmpC beta lactamase gene by performing electrophoresis or by performing a high-performance liquid chromatography analysis technique known as WAVE analysis.

Additionally, a method for identifying different types of ampC beta-lactamase nucleic acid in a clinical sample is also provided. Preferably, the clinical sample provided is characterized as a Gram-negative bacteria with resistance to beta-lactam antibiotics, and the ampC beta-lactamase nucleic acid are of a different origin relative to a bacteria's chromosomal ampC beta-lactamase nucleic acid. The method includes, providing a clinical sample; contacting the clinical sample with at least two pairs of oligonucleotide primers specific for nucleic acid of a particular type of AmpC beta-lactamase gene, wherein one primer of each pair is complementary to at least a portion of the ampC beta-lactamase nucleic acid in the sense strand and the other primer of each pair is complementary to at least a portion of the ampC beta-lactamase nucleic acid in the antisense strand; annealing the primers to the ampC beta-lactamase nucleic acid; simultaneously extending the annealed primers from a 3' terminus of each primer to synthesize an extension product that is complementary to the nucleic acid strands annealed to each primer wherein each extension product after separation from the ampC beta-lactamase nucleic acid serves as a template for the synthesis of an extension product for the other primer of each pair; separating the amplified products; and analyzing the separated amplified products for a size characteristic of the particular type of AmpC beta-lactamase gene.

Also, a method for identifying the presence of plasmid-mediated ampC beta-lactamase nucleic acid in a clinical sample is provided. Preferably the plasmid-mediated ampC beta-lactamase nucleic acid are of a different origin relative to a bacteria's chromosomal ampC beta-lactamase nucleic acid. The method includes, contacting the clinical sample with 2–6 pairs of oligonucleotide primers specific for nucleic acid of plasmid-mediated AmpC beta-lactamase gene, wherein one primer of each pair is complementary to at least a portion of a plasmid-mediated ampC beta-lactamase nucleic acid in the sense strand and the other primer of each pair is complementary to at least a portion of a plasmid-mediated ampC beta-lactamase nucleic acid in the antisense strand; annealing the primers to the plasmid-mediated ampC beta-lactamase nucleic acid, if present; simultaneously extending the annealed primers from a 3' terminus of each primer to synthesize an extension product that is complementary to the nucleic acid strands annealed to each primer, wherein each extension product after separation from the plasmid-mediated ampC beta-lactamase nucleic acid serves as a template for the synthesis of an extension product for the other primer of each pair; and analyzing the sample for amplified products characteristic of a plasmid-mediated AmpC beta lactamase gene. Analyzing the sample may include separating the amplified products and analyzing the separated amplified products for a size characteristic of an AmpC beta-lactamase gene. Further, the primers may be selected from the primer sequences set forth in SEQ ID NOs: 1–12.

The methods described above can employ oligonucleotide primers that may be used for identifying different types of ampC beta-lactamase nucleic acid, as well as for identifying transferable and plasmid-mediated ampC beta-lactamase nucleic acid. Other oligonucleotide primers suitable for use in the methods of the present invention include primers that are specific for AmpC beta-lactamase genes designated as MOX1-2, CMY1, 8-11, LAT1-4, CMY2-7, BIL-1, DHA1-2, ACC-1, MIR-1, ACT-1, and/or FOX 1-5b (FOX 6, see GenBank accession number AY034848).

Further, a diagnostic kit for identifying ampC beta-lactamase nucleic acid in a sample is provided. The diagnostic kit includes, at least two primer pairs capable of hybridizing to a specific type of ampC beta-lactamase nucleic acid; at least one positive control and at least one negative control; and a protocol for identification of the specific type of ampC beta-lactamase nucleic acid of interest. The kit may be used for identifying, preferably, different types of ampC beta-lactamase nucleic acid, more preferably, transferable ampC beta-lactamase nucleic acid, and even more preferably, plasmid-mediated beta-lactamase nucleic acid. The kit may further include the primer pairs individually packaged within the kit.

BRIEF DESCRIPTION OF THE FIGURES

FIG. 5A) Lanes 1–4, 6–8, and 12 are *E. coli* isolates, lanes 5 and 9 are *K. pneumoniae* isolates, lane 10 is a *P. mirabilis* isolate and lane 11 is an *E. aerogenes* isolate. FIG. 5B) Lanes 1, 2, 4, and 10 are *E. coli* isolates, lanes 3 and 5–9 are *K. pneumoniae* isolates. The amplified product from each PCR reaction is indicated on the right, the size of the marker in base pairs is shown on the left.

FIG. 6A. Chromatogram obtained using multiplex PCR products amplified from the following DNA templates (bottom to top): FOX-1, ACT-1, ACC, DHA-1, LAT-1, MOX-1, combination of the six DNA templates listed above, DNA marker pUC 18. FIG. 6B. Agarose gel electrophoresis of multiplex PCR products obtained using 3 different combinations of DNA templates; 2 templates (FOX-1 and ACT-1); 4 templates (MOX-1, LAT-1, DHA-1 and ACC); 6 templates (combination of the six templates listed previously) M, 100-bp ladder. The amplified product from each PCR reaction is indicated on the left, the size of the marker in base pairs is shown on the right.

DETAILED DESCRIPTION OF PREFERRED EMBODIMENTS

Figure 1:
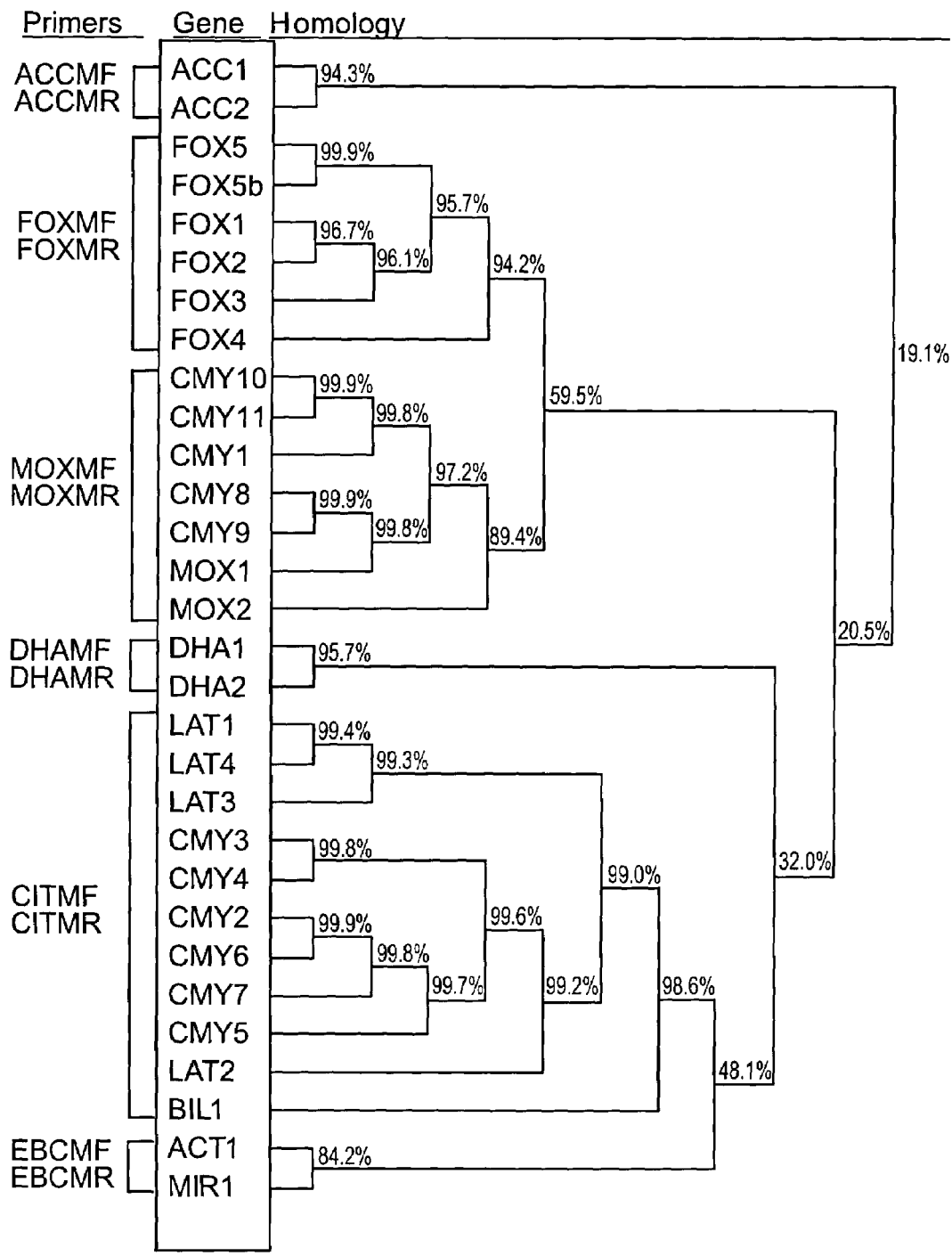
FIG. 1. AmpC dendrogram. Sequences were downloaded from the GenBank database and structural genes were compared, as described in materials and methods, using DNAsis program (Hitachi Software Engineering Co., Ltd., Yokohama, Japan). Bold values correspond to the percent similarity between the most distinct member of each cluster and the other members within that cluster. Primer pairs are correlated by the family of genes they amplify.

In order to detect bacterial pathogens which express AmpC beta-lactamases, clinical microbiologists must have the tools to differentiate organisms expressing ESBLs from organisms expressing AmpC beta-lactamases. There are several phenotypic tests that can distinguish these two resistance mechanisms but even these tests cannot differentiate the different types or families of AmpC beta-lactamases. This differentiation is necessary in order to address epidemiology or hospital infection control. In addition, funding issues in clinical laboratories have reduced the level of expertise and the number of personnel responsible for identifying these resistance mechanisms. Therefore, more clinical laboratories must rely heavily on automated susceptibility testing. The use of automated systems, while adequate for less complicated organisms, are not adequate for the newer generation of antibiotic resistant bacteria. These are bacteria with multiple resistance mechanisms, many of which have multiple beta-lactamases. Automated systems can only be as good as the mathematical algorithms used to program the system. As the combination of resistance mechanisms found in bacteria becomes more and more complicated, the people involved in developing these programs will find it more difficult to update these programs. One example of this is found with the identification of AmpC-mediated resistance. A recent study found that the AmpC-resistance mechanism was incorrectly identified as an ESBL plus an impermeability mutation by an automated antimicrobial susceptibility test system (Sanders et al., *J. Clin. Microbiol.*, 38(2):570–574 (2000)).

Twenty-nine different ampC genes have been identified to date. None of these genes can be distinguished by phenotypic testing. Understanding the epidemiology of these resistance mechanisms and the needs of hospital infection control warrants the identification of these genes. Diagnostic testing is desperately needed to identify the presence of AmpC beta-lactamases in clinical isolates. The present invention is useful for a variety of purposes, for example, distinguishing the presence of ESBL from AmpC producing organisms within one organism, and preferably, to detect AmpC beta-lactamases, more preferably to detect transferable AmpC beta-lactamases, and even more preferably, to detect plasmid-mediated AmpC beta-lactamases in organisms which produce chromosomal AmpC beta-lactamases.

The present invention is directed to methods for identifying the presence or absence of an AmpC beta-lactamase gene in a clinical sample, and for identifying different types of, preferably, ampC beta-lactamase nucleic acid, more preferably, transferable ampC beta-lactamase nucleic acid, and even more preferably, plasmid-mediated ampC beta-lactamase nucleic acid, in a clinical sample that are of a different origin relative to the bacteria's chromosomal ampC nucleic acid, particularly Gram-negative bacteria, using multiplex polymerase chain reaction. The method for identifying the presence or absence of an AmpC beta-lactamase in a clinical sample includes providing a clinical sample; contacting the clinical sample with at least two pairs of oligonucleotide primers specific for the nucleic acid of an AmpC beta-lactamase gene, wherein one primer of the at least two pairs is complementary to at least a portion of the ampC beta-lactamase nucleic acid in the sense strand and the other primer of each pair is complementary to at least a portion of the ampC beta-lactamase nucleic acid in the antisense strand; annealing the primers to the ampC beta-lactamase nucleic acid, if the nucleic acid is present in the sample; simultaneously extending the annealed primers from a 3' terminus of each primer to synthesize an extension product that is complementary to the nucleic acid strands annealed to each primer wherein each extension product after separation from the ampC beta-lactamase nucleic acid, if present, serves as a template for the synthesis of an extension product for the other primer of each pair; and analyzing the sample for the presence or absence of amplified products. The presence of amplified products indicates the presence of an AmpC beta-lactamase gene in the sample. Analysis of the sample may include separating amplified products from the sample and analyzing the products for a size characteristic of a particular type of AmpC beta-lactamase gene using electrophoresis or WAVE analysis.

The method may also be used for identifying different types of ampC beta-lactamase nucleic acid in a clinical sample. The method is performed as indicated above, using at least two pairs of oligonucleotide primers specific for a particular type of AmpC beta-lactamase gene and analyzing the amplified products for a size characteristic of the particular type of AmpC beta-lactamase gene. The method may further be used to identify the presence of plasmid-mediated ampC beta-lactamase nucleic acid in a clinical sample by the method indicated above. By this method, the sample is contacted with 2–6 pairs of primers specific for nucleic acid of plasmid-mediated AmpC beta-lactamase gene. The sample is then analyzed for amplified products characteristic of a plasmid-mediated AmpC beta-lactamase gene.

The method involves the use of at least two primer pairs, preferably at least 3 primer pairs, more preferably at least 4 primer pairs, even more preferably at least five primer pairs, and most preferably at least 6 primer pairs in a multiplex polymerase chain reaction (PCR) for the detection of family-specific ampC beta-lactamase genes. In performing the multiplex PCR technique, primers were designed from known ampC beta-lactamase nucleic acid, such as those submitted to GenBank (Table 3). Preferably, this amplification method relates to the treatment of a sample containing ampC beta-lactamase nucleic acid (preferably, deoxyribose nucleic acid (DNA)), from bacteria, particularly Gram-negative bacteria, with a molar excess of each primer of the oligonucleotide primer pairs, heating the sample containing the ampC beta-lactamase nucleic acid to yield two single-stranded complementary nucleic acid strands, adding the primer pairs to the sample containing the ampC beta-lactamase nucleic acid strands, allowing each primer to anneal to a particular strand under appropriate temperature conditions that permit hybridization, providing molar excesses of nucleotide triphosphates and polymerase to extend each primer to form a complementary extension product that can be employed in amplification of ampC beta-lactamase nucleic acid, detecting the amplified nucleic acid, if ampC beta-lactamase nucleic acid was present in the sample, and analyzing the amplified nucleic acid. The amplified nucleic acid may be analyzed for a size specific amplicon (as indicated below in Table 3) characteristic of a specific ampC beta-lactamase nucleic acid. This process of heating, annealing, and synthesizing is repeated many times, and with each cycle the ampC beta-lactamase nucleic acid increases in abundance. Within a short period of time, it is possible to obtain a specific ampC beta-lactamase nucleic acid, e.g., a DNA molecule that can be readily purified and identified.

This technique is capable of detecting the presence or absence of, and, if present, identifying the family-specific ampC gene responsible for AmpC beta-lactamase expression. In addition, this technique can be used to detect ampC genes in organisms expressing a chromosomal AmpC beta-lactamase as long as the ampC gene is not from the same chromosomal origin. The strategy and parameters of the multiplex PCR are described below.

Conventional phenotypic methods used to detect isolates expressing AmpC beta-lactamases have restricted detection of this resistance mechanism to mainly organisms without an inducible chromosomal ampC gene such as *K. pneumoniae, Salmonella typhimurium*, or *E. coli*. In the case of *K. pneumoniae* and *S. typhimurium*, no chromosomal gene is present; therefore, there is no endogenous AmpC beta-lactamase to interfere with either susceptibility testing or hydrolysis assays. Normally, *E. coli* produces its chromosomal ampC gene at a low constitutive level, which has little influence on susceptibility testing or beta-lactamase hydrolysis assays. However, perturbations in the regulation of *E. coli* AmpC production resulting in hyperproduction of AmpC beta-lactamase requires molecular tests in order to verify the presence or absence of transferable ampC genes. The discriminatory power of the ampC multiplex PCR technique between the presence of known transferable ampC genes and a putative hyperproducing *E. coli* strain has been more fully described below.

This diagnostic method can also discriminate between transferable ampC genes in organisms coding for inducible AmpC beta-lactamases so long as they are not of the same origin. Because ampC genes originated from chromosomal genes, there is a possibility that a bacteria, preferably a Gram-negative bacteria, containing chromosomal ampC beta-lactamase nucleic acid and ampC beta-lactamase having a common origin, will cross-hybridize and amplify a product from the chromosomal ampC beta-lactamase nucleic acid. Thus, preferably, ampC multiplex PCR is used on samples containing ampC beta-lactamase nucleic acid of a different origin as compared to that of the chromosomal ampC beta-lactamase, in the event the bacteria contains a chromosomal ampC beta-lactamase.

An oligonucleotide primer pair includes one primer that is substantially complementary to at least a portion of a sense strand of a known ampC beta-lactamase nucleic acid and one primer that is substantially complementary to at least a portion of an antisense strand of a known ampC beta-lactamase nucleic acid. The process of forming extension products preferably involves simultaneously extending the annealed primers from a 3' terminus of each primer to synthesize an extension product that is complementary to the nucleic acid strands annealed to each primer wherein each extension product after separation from the ampC beta-lactamase nucleic acid serves as a template for the synthesis of an extension product for the other primer of each pair. The amplified products are typically detected by size fractionization using gel electrophoresis, but can also be separated by size exclusion using other techniques, such as a high-performance liquid chromatography (HPLC)-based system known as the WAVE Nucleic Acid Fragment Analysis System (Transgenomic, Inc., Omaha, Nebr.). WAVE uses a HPLC-based system in conjunction with single and double stranded polynucleotide separation processes to provide separations in less time than required for gel electrophoresis without significant loss of specificity and sensitivity, and typically increases sensitivity.

An "oligonucleotide," as used herein, refers to a polymeric form of nucleotides of any length, either ribonucleotides or deoxyribonucleotides. The term oligonucleotide refers particularly to the primary structure, and thus includes double and single-stranded DNA molecules and double and single-stranded RNA molecules.

A "primer," as used herein, is an oligonucleotide that is complementary to at least a portion of an ampC beta-lactamase nucleic acid and, after hybridization to the nucleic acid, may serve as a starting-point for the polymerase chain reaction. The terms "primer" or "oligonucleotide primer," as used herein, further refer to a primer having a nucleotide sequence that possesses a high degree of nucleic acid sequence similarity to at least a portion of the ampC beta-lactamase nucleic acid. "High degree" of sequence similarity refers to a primer that typically has at least about 80% nucleic acid sequence similarity, and preferably at least about 90% nucleic acid sequence similarity. Sequence similarity may be determined, for example, using sequence techniques such as GCG FastA (Genetics Computer Group, Madison, Wis.), MacVector 4.5 (Kodak/IBI software package) or other suitable sequencing programs or methods known in the art.

The terms "complement" and "complementary," as used herein, refer to a nucleic acid that is capable of hybridizing to a specified nucleic acid molecule under stringent hybridization conditions. Stringent hybridization conditions include, for example, temperatures from about 50 degrees Celsius (° C.) to about 65° C., and magnesium chloride ($MgCl_2$) concentrations from about 1.5 millimolar (mM) to about 2.0 mM. Thus, a specified DNA molecule is typically "complementary" to a nucleic acid if hybridization occurs between the specified DNA molecule and the nucleic acid. If the specified DNA molecule hybridizes to the full length of the nucleic acid molecule, then the specified DNA molecule is typically a "full-length complement." "Complementary," further refers to the capacity of purine and pyrimidine nucleotides to associate through hydrogen bonding in double stranded nucleic acid molecules. The following base pairs are complementary: guanine and cytosine; adenine and thymine; and adenine and uracil.

The terms "compatible" and, "compatibility," as used herein, refer to the ability of the primers to be mixed together such that no primers cause any type of significant interference with each other. It is requisite for the primers used in multiplex reactions to be highly compatible so that they may be used together in the same reaction mixture without significant interference from one another.

As used herein, the terms "amplified molecule," "amplified fragment," and "amplicon" refer to a nucleic acid molecule (typically, DNA) that is a copy of at least a portion of the nucleic acid and its complementary sequence. The copies correspond in nucleotide sequence to the original molecule and its complementary sequence. The amplicon can be detected and analyzed by a wide variety of methods. These include, for example, gel electrophoresis, single strand conformational polymorphism (SSCP), restriction fragment length polymorphism (RFLP), capillary zone electrophoresis (CZE), an HPLC-based nucleic acid analyzing technology known as WAVE, microchip detection methods, and the like. Preferably, the amplicon can be detected, and hence, the type of ampC beta-lactamase nucleic acid identified, using gel electrophoresis and appropriately sized markers, according to techniques known to one of skill in the art.

The primers are oligonucleotides, either synthetic or naturally occurring, capable of acting as a point of initiating synthesis of a product complementary to the size of the DNA molecule containing an ampC beta-lactamase nucleic acid. The primer includes nucleotides capable of hybridizing under stringent conditions to at least a portion of at least one strand of a nucleic acid molecule of a given ampC beta-lactamase. Preferably, the primers of the present invention typically have at least about 15 nucleotides. Preferably, the primers have no more than about 35 nucleotides, and more preferably, no more than about 25 nucleotides. The primers are chosen such that they preferably produce a primed product of about 200–1100 base pairs.

Optionally, a primer used in accordance with the present invention includes a label constituent. The label constituent can be selected from the group of an isotopic label, a fluorescent label, a polypeptide label, and a dye release compound. The label constituent is typically incorporated in the primer by including a nucleotide having the label attached thereto. Isotopic labels preferably include those compounds that are beta, gamma, or alpha emitters, more preferably isotopic labels are selected from the group of $^{32}P$, $^{35}S$, and $^{125}I$. Fluorescent labels are typically dye compounds that emit visible radiation in passing from a higher to a lower electronic state, typically in which the time interval between adsorption and emission of energy is relatively short, generally on the order of about $10^{-8}$ to about $10^{-3}$ second. Suitable fluorescent compounds that can be utilized include fluorescien and rhodamine, for example. Suitable polypeptide labels that can be utilized in accordance with the present invention include antigens (e.g., biotin, digoxigenin, and the like) and enzymes (e.g., horseradish peroxidase). A dye release compound typically includes chemiluminescent systems defined as the emission of absorbed energy (typically as light) due to a chemical reaction of the components of the system, including oxyluminescence, in which light is produced by chemical reactions involving oxygen.

Preferred examples of these primers that are specific for certain ampC beta-lactamases are as follows, wherein "F" in the designations of the primers refers to a 5' upstream primer and "R" refers to a 3' downstream primer. Typically, hybridization conditions utilizing at least two primer pairs of the invention include, for example, a hybridization temperature of about 50° C. to about 65° C., and a $MgCl_2$ concentration of about 1.5 mM to about 2.0 mM. Although lower temperatures and higher concentrations of $MgCl_2$ can be employed, this may result in decreased primer specificity.

The following primers are specific for nucleic acid characteristic of the AmpC beta-lactamases designated as MOX1, MOX2 and CMY1, 8-11, and their chromosomal origin.

```
Primer Name: MOXMF
Primer Sequence:
5' -GCTGCTCAAGGAGCACAGGAT -3'     (SEQ ID NO:1)

Primer Name: MOXMR
Sequence Name:
5' -CACATTGACATAGGTGTGGTGC -3'    (SEQ ID NO:2)
```

Employing a primer pair containing the primer sequences of SEQ ID NO:1 and SEQ ID NO:2 to a sample containing AmpC beta-lactamases designated as MOX1-2 and CMY1, 8-11, a size-specific amplicon of 520 base pairs will typically be obtained.

The following primers are specific for nucleic acid characteristic of the AmpC beta-lactamases designated as LAT1-4, CMY2-7, and BIL-1, and their chromosomal origin.

```
Primer Name: CITMF
Primer Sequence:
5' -TGGCCAGAACTGACAGGCAAA -3'     (SEQ ID NO:3)

Primer Name: CITMR
Primer Sequence:
5' -TTTCTCCTGAACGTGGCTGGC -3'     (SEQ ID NO:4)
```

Employing a primer pair containing the primer sequences of SEQ ID NO:3 and SEQ ID NO:4 to a sample containing AmpC beta-lactamases designated as LAT 1-4, CMY2-7, and BIL-1, a size-specific amplicon of 462 base pairs will typically be obtained.

The following primers are specific for nucleic acid characteristic of the AmpC beta-lactamases designated as DHA1-2, and their chromosomal origin.

```
Primer Name: DHAMF
Primer Sequence:
5' -AACTTTCACAGGTGTGCTGGGT -3'    (SEQ ID NO:5)

Primer Name: DHAMR
Primer Sequence:
5' -CCGTACGCATACTGGCTTTGC -3'     (SEQ ID NO:6)
```

Employing a primer pair containing the primer sequences of SEQ ID NO:5 and SEQ ID NO:6 to a sample containing AmpC beta-lactamases designated as DHA1-2, a size-specific amplicon of 405 base pairs will typically be obtained.

The following primers are specific for nucleic acid characteristic of the AmpC beta-lactamases designated as ACC-1, and their chromosomal origin.

```
Primer Name: ACCMF
Primer Sequence:
5' -AACAGCCTCAGCAGCCGGTTA-3'      (SEQ ID NO:7)

Primer Name: ACCMR
Primer Sequence:
5' -TTCGCCGCAATCATCCCTAGC -3'     (SEQ ID NO:8)
```

Employing a primer pair containing the primer sequences of SEQ ID NO:7 and SEQ ID NO:8 to a sample containing AmpC beta-lactamases designated as ACC-1, a size-specific amplicon of 346 base pairs will typically be obtained.

The following primers are specific for nucleic acid characteristic of the AmpC beta-lactamases designated as MIR-1 and ACT-1, and their chromosomal origin.

```
Primer Name: EBCMF
Primer Sequence:
5' -TCGGTAAAGCCGATGTTGCGG -3'     (SEQ ID NO:9)

Primer Name: EBCMR
Primer Sequence:
5' -CTTCCACTGCGGCTGCCAGTT -3'     (SEQ ID NO:10)
```

Employing a primer pair containing the primer sequences of SEQ ID NO:9 and SEQ ID NO: 10 to a sample containing AmpC beta-lactamases designated as MIR-1 and ACT-1, a size-specific amplicon of 302 base pairs will typically be obtained.

The following primers are specific for nucleic acid characteristic of the AmpC beta-lactamases designated as FOX1-5b (FOX 6, see GenBank accession number AY034848), and their chromosomal origin.

```
Primer Name: FOXMF
Primer Sequence:
5' -AACATGGGGTATCAGGGAGATG -3'    (SEQ ID NO:11)

Primer Name: FOXMR
Primer Sequence:
5' -CAAAGCGCGTAACCGGATTGG -3'     (SEQ ID NO:12)
```

Employing a primer pair containing the primer sequences of SEQ ID NO:11 and SEQ ID NO:12 to a sample containing AmpC beta-lactamases designated as FOX1-5b (FOX 6, see GenBank accession number AY034848), a size-specific amplicon of 190 base pairs will typically be obtained.

Various other primers, or variations of the primers described above, can also be prepared and used according to methods of the present invention. For example, alternative primers can be designed based on targeted ampC beta-lactamases known or suspected to contain regions possessing high G/C content (i.e., the percentage of guanine and cytosine residues). As used herein, a "high G/C content" in a target nucleic acid, typically includes regions having a percentage of guanine and cytosine residues of about 60% to about 90%. Thus, changes in a prepared primer will alter, for example, the hybridization or annealing temperatures of the primer, the size of the primer employed, and the sequence of the specific resistance gene or nucleic acid to be identified. Therefore, manipulation of the G/C content, e.g., increasing or decreasing, of a primer or primer pair may be beneficial in increasing detection sensitivity in the method.

Additionally, depending on the suspected ampC beta-lactamase nucleic acid in the sample, a primer of the invention can be prepared that varies in size. Preferably, primers of the invention are about 15 nucleotides to about 35 nucleotides in length, more preferably the primers are about 15 nucleotides to about 25 nucleotides in length. Oligonucleotides of the invention can readily be synthesized by techniques known in the art (see, for example, Crea et al., Proc. Natl. Acad. Sci. (U.S.A.), 75:5765 (1978)).

Once the primers are designed, their specificity can be tested using the following method. Depending on the ampC beta-lactamase nucleic acid of clinical interest, a nucleic acid is isolated from a bacterial control strain known to express or contain the resistance gene. This control strain, as used herein, refers to a "positive control" nucleic acid (typically, DNA). Additionally, a "negative control" nucleic acid (typically, DNA) can be isolated from one or more bacterial strains known to express a resistance gene other than the target gene of interest. Using the polymerase chain reaction, the designed primers are employed in a detection method, as described above, and used in the positive and negative control samples and in at least one test sample suspected of containing the resistance gene of interest. The positive and negative controls provide an effective and qualitative (or grossly quantitative) means by which to establish the presence or the absence of the gene of interest of test clinical samples. It should be recognized that with a small percentage of primer pairs, possible cross-reactivity with other beta-lactamase genes might be observed. However, the size and/or intensity of any cross-reactive amplified product will be considerably different and can therefore be readily evaluated and dismissed as a negative result.

The invention also relates to kits for identifying, preferably, different types of ampC beta-lactamase nucleic acid, more preferably, transferable ampC beta-lactamase nucleic acid, and even more preferably, plasmid-mediated ampC beta-lactamase nucleic acid, by multiplex PCR analysis. Kits of the invention typically include, but are not limited to, at least two primer pairs capable of hybridizing to a specific type of ampC beta-lactamase nucleic acid, one or more positive controls, one or more negative controls, and a protocol for identification of the specific type of ampC beta-lactamase nucleic acid of interest using multiplex PCR. A negative control includes a nucleic acid (typically, DNA) molecule encoding a resistant ampC beta-lactamase other than an ampC beta-lactamase. The negative control nucleic acid may be a naked nucleic acid (typically, DNA) molecule or inserted into a bacterial cell. Preferably, the negative control nucleic acid is double stranded, however, a single stranded nucleic acid may be employed. A positive control includes a nucleic acid (typically, DNA) that encodes an ampC beta-lactamase from the suspected ampC beta-lactamase. The positive control nucleic acid may be a naked nucleic acid molecule or inserted into a bacterial cell, for example. Preferably, the positive control nucleic acid is double stranded, however, a single stranded nucleic acid may be employed. Typically, the nucleic acid is obtained from a bacterial lysate. Protocols include, for instance, such conditions as primer concentration, buffer concentration, magnesium chloride concentration, hybridization temperature, and the number of PCR cycles appropriate to the identification of ampC beta-lactamase nucleic acid.

Accordingly, the present invention provides a kit for characterizing and identifying, preferably, an AmpC beta-lactamase, more preferably, a transferable AmpC beta-lactamase nucleic acid, and even more preferably, a plasmid-mediated AmpC beta-lactamase, that would have general applicability. Preferably, the kit includes a polymerase (typically, DNA polymerase) enzyme, such as Taq polymerase, and the like. A kit of the invention also preferably includes at least two primer pairs that are specific for at least two different ampC beta-lactamases. A buffer system compatible with the polymerase enzyme is also included and is well known in the art. Optionally, the at least two primer pairs may contain a label constituent, a fluorescent label, a polypeptide label, and a dye release compound. The kit may further contain at least one internal sample control, in addition to one or more further means required for multiplex PCR analysis, such as a reaction vessel. If required, a nucleic acid from the bacterial sample can be isolated and then subjected to multiplex PCR analysis using the at least two provided primer sets of the invention.

In another embodiment, AmpC beta-lactamase genes in clinical samples, particularly clinical samples containing Gram-negative bacteria, can be detected by the primers described herein in a "microchip" detection method. In a microchip detection method, nucleic acid, e.g., genes, of multiple AmpC beta-lactamases in clinical samples can be detected with a minimal requirement for human intervention. Techniques borrowed from the microelectronics industry are particularly suitable to these ends. For example, micromachining and photolithographic procedures are capable of producing multiple parallel microscopic scale components on a single chip substrate. Materials can be mass produced and reproducibility is exceptional. The microscopic sizes minimize material requirements. Thus, human manipulations can be minimized by designing a microchip type surface capable of immobilizing a plurality of primers of the invention on the microchip surface.

Microchip detection methods generally include the formation of high-density arrays of, for example, oligonucleotides on a surface, typically glass, that can then be used for various applications, such as large scale hybridization (Roth et al., *Annu. Rev. Biomed. Eng.*, 1:265–297 (1999)). Using this method, applications using two types of nucleic acids as targets, synthesizing or printing directly on a surface, or covalent or noncovalent attachment of single stranded cDNA, are known.

According to one of the methods of microchip detection, arrays of short oligonucleotides may be synthesized directly on a surface, such as glass, using methods generally known in solid-phase chemistry synthesis. This is generally accomplished by either masking most of the array, activating the unmasked portion, and adding a phosphoramidite to produce a coupling to the 5'-hydroxy groups of the activated segments of the array or by printing the arrays directly on the surface using ink jet printing techniques.

Alternatively, for production of longer sequences, such as cDNA arrays, a spotting method for attaching molecules to a surface may be used. In this method, for instance, sequences are created from clones, purified, and optionally amplified. The sequences are then attached noncovalently to a glass surface by coating the surface with polylysine or by chemically treating it with an aminosilane to make it cationic. Attachment of the sequences under this method are generally nonspecific and may involve multiple attachment sites along the molecule. An additional method known for attachment of sequences to a surface is to covalently attach amino-modified cDNA, produced by asymmetric PCR, to silylated glass using sodium borohydhydride (Roth et al., *Annu. Rev. Biomed. Eng.*, 1:265–297 (1999)).

Thus, an object of the present invention is to provide a parallel screening method wherein multiple serial reactions are automatically performed individually within one reaction well for each of the plurality of nucleic acid strands to be detected in the plural parallel sample wells. These serial reactions are performed in a simultaneous run within each of the multiple parallel lanes of the device. "Parallel" as used herein means wells identical in function. "Simultaneous" means within one preprogrammed run. The multiple reactions automatically performed within the same apparatus minimize sample manipulation and labor.

Thus, the present invention provides multiple reaction wells, the reaction wells being reaction chambers, on a microchip. Each reaction well contains an individualized array to be used for detecting a beta-lactamase gene uniquely specified by the substrates provided, the reaction conditions, and the sequence of reactions in that well. The chip can thus be used as a method for identifying beta-lactamase genes in clinical samples.

There have been no reports of clinical isolates expressing more than one AmpC beta-lactamase. Two reasons that could explain this observation are: 1) the inability to accurately detect the presence of transferable AmpC beta-lactamases does not allow for the detection of multiple AmpC genes, and 2) there is a limit to the amount of AmpC beta-lactamase a bacterial cell can accommodate and still be a viable pathogen. The ampC multiplex PCR technique described herein will help to determine the presence of multiple types of transferable AmpC genes that can occur in bacterial isolates.

The limitation for any molecular diagnostic test is that identification is based on known genes or sequences. Thus, all molecular tests suffer from possible false negative results. Sensitivity in detection and PCR conditions can play a role in the ability to decrease the number of false negative results. WAVE analysis using products generated from the ampC multiplex PCR of the present invention are able to detect all six amplicons within one sample. Electrophoresis and ethidium bromide staining typically detect only four different templates at a time, which, however, is still advantageous. Therefore, instruments, such as the WAVE, can be beneficial not only as a time saving device but also for increasing the sensitivity of this assay.

Objects and advantages of this invention are further illustrated by the following examples, but the particular materials and amounts thereof recited in these examples, as well as other conditions and details, should not be construed to unduly limit this invention.

EXAMPLES

Materials and Methods

Bacterial strains. Bacterial strains used as controls in this study are listed in Table 1 shown below. Strains previously identified for the expression of specific plasmid-mediated ampC genes are listed as plasmid-mediated. Strains used as controls to examine the extent of cross-hybridization for specific primers with chromosomal ampC genes are listed as chromosomal. In addition, 22 clinical isolates were evaluated for the presence of plasmid-mediated ampC genes in this study. These isolates included 18 isolates of *E. coli* (7 of which are known controls and are listed in Table 1), 8 of *K. pneumoniae*, 2 of *P. mirabilis*, and one of *E. aerogenes*.

TABLE 1

Bacterial Strains

| Strain | Organism | AmpC |
| --- | --- | --- |
| Plasmid-Mediated | | |
| MISC 340 | *Klebsiella pneumoniae* | FOX-1 |
| MISC 393 | *Escherichia coli* | FOX-3 |
| MISC 416 | *Escherichia coli* | FOX-4 |
| MHM 2 | *Klebsiella pneumoniae* | FOX-5 |
| COUD M 621 | *Klebsiella pneumoniae* | FOX-5b (FOX 6, see GenBank accession no. AY034848 |
| MISC 341 | *Klebsiella pneumoniae* | LAT-1 |
| MISC 368 | *Escherichia coli* | LAT-2 |
| KLEB 249 | *Klebsiella pneumoniae* | CMY-2 |
| SAL 100 | *Salmonella thyphimurium* | CMY-7 |
| MISC 345 | *Escherichia coli* | BIL-1 |
| MISC 339 | *Klebsiella pneumoniae* | MOX-1 |
| MISC 380 | *Escherichia coli* | DHA-1 |
| MISC 304 | *Klebsiella pneumoniae* | MIR-1 |
| KLEB 225 | *Klebsiella pneumoniae* | ACT-1 |
| Chromosomal | | |
| JW 3 | *Hafnia alvei* | Wild type |
| ENTB 7 | *Enterobacter cloacae* | Wild type |
| GB 52 | *Citrobacter* spp. | Wild type |
| CIN 6 | *Pseudomonas aeruginosa* | Wild type |
| SERR 1 | *Serratia marcescens* | Wild type |
| MORG 103 | *Morganella morganii* | Wild type |
| KLEB 23 | *Klebsiella pneumoniae* | Wild type |
| HB 101 | *Escherichia coli* | Wild type |
| VITEK 109492 | *Escherichia coli* | hyperproducer mutant |

Preparation of template DNA. The organisms were inoculated into 5 milliliters (ml) of Luria-Bertani broth (Difco, Detroit, Mich.) and incubated for 20 hours at 37 degrees Celsius (° C.) with shaking. Cells from 1.5 ml of an overnight culture were harvested by centrifugation at 17,310×g for 5 minutes. After the supernatant was decanted, the pellet was resuspended in 500 microliters (µl) of distilled water. The cells were lysed by heating at 95° C. for 10 minutes, and cellular debris was removed by centrifugation at 17,310×g for 5 minutes. The supernatant (1/250th volume) was used as a source of template for amplification.

PCR protocol. PCR was performed in a final volume of 50 µl in 0.5 ml thin-walled tubes. Each reaction contained: 20 mM TRIS-HCL (pH 8.4), 50 mM KCl, 0.2 mM of each deoxynucleoside triphosphate, 1.5 mM magnesium chloride ($MgCl_2$), 0.6 micromolar (µM) of primers MOXMF, MOXMR, CITMF, CITMR, DHAMF and DHAMR, 0.5 µM of primers ACCMF, ACCMR, EBCMF, and EBCMR, 0.4 µM of primers FOXMF and FOXMR, and 1.25 units of Taq DNA polymerase (Life Technologies, Rockville, Md.). Template DNA (2 µl) was added to 48 µl of master mix and then overlaid with mineral oil. The PCR program consisted of an initial denaturation step at 94° C. for 3 minutes, followed by 25 cycles of DNA denaturation at 94° C. for 30 seconds, primer annealing at 64° C. for seconds, and primer extension at 72° C. for 1 minute. After the last cycle a final extension step at 72° C. for 7 minutes was added. Five microliter aliquots of PCR product were analyzed by agarose gel electrophoresis using 2% agarose (BioRad, Hercules, Calif.). Gels were stained with ethidium bromide at 10 microgram per milliliter (µg/ml) and visualized by UV transillumination.

WAVE. The Wave Nucleic Acid Fragment Analysis System (Transgenomics, Inc., Omaha, Nebr.) was used to reduce the total time required for separation and visualization of the PCR products, as compared with using gel electrophoresis. The WAVE technology uses a matched ion polynucleotide chromatography process using separation media having a non-polar surface, wherein the process uses a counterion agent and an organic solvent to release polynucleotides from the separation media (U.S. Pat. No. 6,210,885). The WAVE systems are equipped with computer controlled ovens which enclose the columns and column inlet areas (U.S. Pat. No. 6,210,885) and utilize proprietary WAVEMAKER software (Transgenomics, Inc., Omaha, Nebr.).

A comparison of the methods of gel electrophoresis and WAVE technology (FIGS. 6A and 6B) was performed using ampC multiplex PCR products from representative members of each ampC family. WAVE analysis was performed using WAVE system Model Number 2100 and WAVEmaker 4.1 software (Transgenomics, Inc., Omaha, Nebr.). Samples are taken automatically by an autosampler in the WAVE system using parameters set by the operator prior to sampling. The parameters used in the analysis are set forth in Table 2:

TABLE 2

WAVE Gradient Parameters

| Step[a] | Time (min)[b] | % Buffer A[c] | % Buffer B[d] | % Buffer D[e] |
| --- | --- | --- | --- | --- |
| Loading | 0.0 | 51 | 49 | 0 |
| Step 1 | 0.5 | 46 | 54 | 0 |
| Step 2 | 1.0 | 42 | 58 | 0 |
| Step 3 | 1.5 | 40 | 60 | 0 |
| Step 4 | 2.5 | 38 | 62 | 0 |
| Step 5 | 3.5 | 37 | 63 | 0 |
| Step 6 | 4.5 | 37 | 63 | 0 |
| Step 7 | 5.5 | 34 | 66 | 0 |
| Step 8 | 6.5 | 32 | 68 | 0 |
| Start Clean | 6.6 | 0 | 0 | 100 |
| Stop Clean | 7.1 | 0 | 0 | 100 |
| Start Equilibrate | 7.2 | 51 | 49 | 0 |
| Stop Equilibrate | 8.1 | 51 | 49 | 0 |

[a]The sequence of events for loading, gradient changes, and cleaning the column.
[b]The time of each gradient change.
[c]0.1 M triethylammonium acetate (TEAA)
[d]0.1 M TEAA, 25% acetonitrile.
[e]75% acetonitrile

Results

Dendrogram and primer design. The genes encoding AmpC beta-lactamases are of chromosomal origin, derived from members of the family Enterobacteraceae. To date, twenty-nine different AmpC beta-lactamases have been identified (FIG. 1). They can be grouped based on their chromosomal origin. For example, the genes encoding the AmpC beta-lactamases LAT-1, CMY-2 and BIL-1 are 90.4% similar to chromosomal ampC gene of *Citrobacter freundii* strain OS60. The ability to group different ampC genes allows evaluation of similarity clusters. A high degree of similarity within these clusters can result in the design of primers capable of amplifying family-specific genes. Thirty sequences of different ampC genes were downloaded from the GenBank database and percent similarities analyzed using DNAsis 2.6 program (Hitachi Software Engineering Co. Ltd., Yokohama, Japan) (FIG. 1). Six different groups were identified based on percent sequence similarity. These groups include ACC (origin *Hafnia alvei*), FOX (origin unknown), MOX (origin unknown), DHA (origin *Morganella morganii*), CIT (origin *Citrobacter freundii*) and EBC (origin *Enterobacter cloacae*). Sequences of each cluster were aligned with the CLUSTAL W multiple alignment option in the MacVector 6.5 program (Accelrys (formerly Oxford Molecular Ltd.), Princeton, N.J.) set at default parameters, and aligned sequences were used as a reference for primer design. The resulting primers were compared with all members of the different clusters in order to avoid cross hybridization. In addition, primers were evaluated for individual melting temperatures ($T_m$) and length. Variation between the individual primers was a $T_m$ of 0.5° C. and a length of 2 nucleotides. The theoretical formation of primer dimers was also evaluated and found insignificant. The twelve primers designed for multiplex PCR are listed in Table 3.

Figure 3:
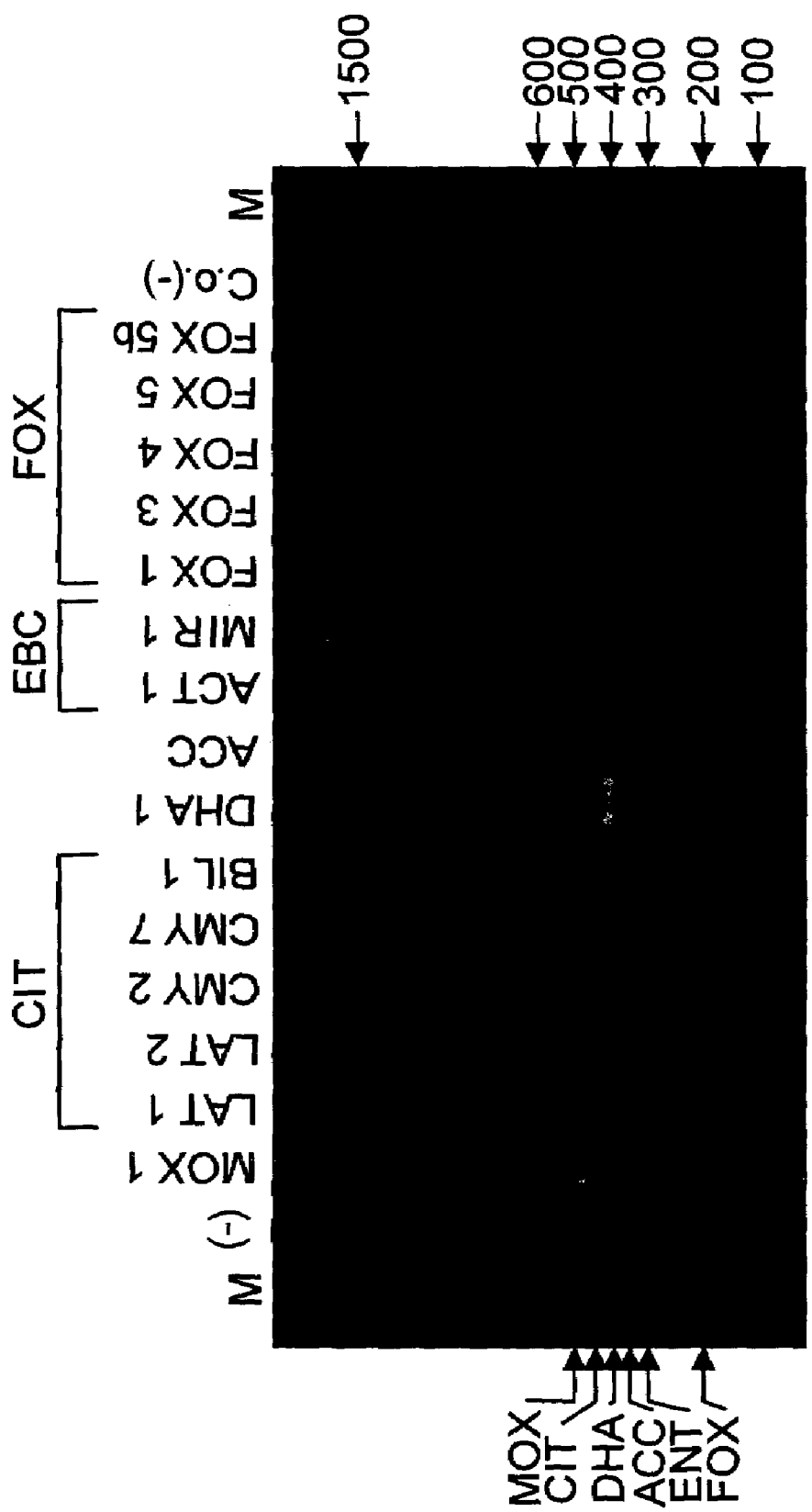
FIG. 3. Resolution of family-specific variation. Multiplex PCR products were separated in a 2% agarose gel. Lanes are labeled with the ampC gene used as template DNA; ACC represents the chromosomal ampC gene from *Hafnia alvei*; (M) 100 bp DNA ladder (Life Technologies, Rockville, Md.); (−) negative water control; (C.o. (−)) carry over negative control. The amplified product from each PCR reaction is indicated on the left, the size of the marker in base pairs is shown on the right.

Multiplex PCR. The compatibility of all six primer pairs were tested using the conditions described above. Each reaction contained all six primer sets and template DNA from a representative member of each of the ampC groups previously described: $bla_{MOX-1}$, $bla_{LAT-1}$, $bla_{DHA-1}$, $bla_{ACC-2}$, $bla_{ACT-1}$ and $bla_{FOX-1}$. As shown in FIG. 3, only one amplification product was observed for each template, and the size observed was consistent with the expected size shown in Table 3 below.

1). In order to demonstrate that sequence variation of individual family members did not influence the outcome of multiplex ampC PCR, different members of each family were used as template (FIG. 3). Amplification of products for each family member of a particular set resulted in a single amplicon of the predicted size. For example, every template of the CIT family resulted in an amplicon of 462 base pairs (FIG. 3).

Figure 4:
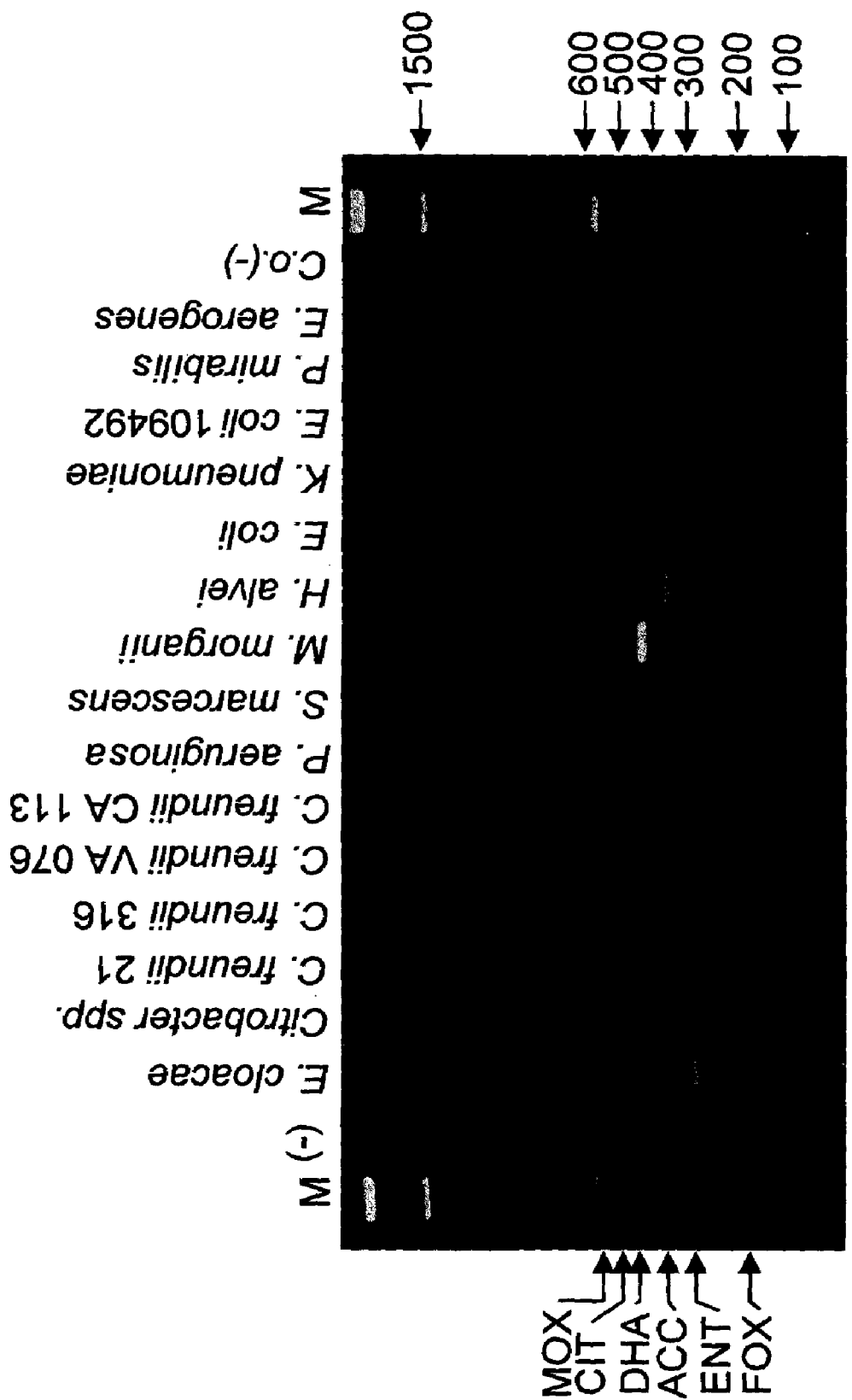
FIG. 4. Evaluation of chromosomal cross-hybridization. Multiplex PCR products were separated in a 2% agarose gel. Lanes are labeled with the name of the organism used as the source of template DNA (Table 1). (M) 100 bp DNA ladder (Life Technologies, Rockville, Md.); (−) negative water control; (C.o. (−)) carry over negative control. The amplified product from each PCR reaction is indicated on the left, the size of the marker in base pairs is shown on the right.

Chromosomal ampC harboring control strains analysis. Due to the mobility of ampC beta-lactamases, any technique aimed to detect these genes requires its use in different genetic backgrounds, including organisms with chromosomal ampC genes, such as *E. cloacae* and *C. freundii*. Because ampC genes originated from chromosomal genes, the ampC multiplex PCR was tested for the possibility of cross-hybridization with chromosomal beta-lactamase genes of different origin. Multiplex PCR was conducted on the Chromosomal organisms listed in Table 1. No amplification was observed using DNA template from *K. pneumoniae, E. coli, P. aeruginosa, S. marcescens, P. mirabilis,* or *E. aerogenes* (FIG. 4). As expected, amplification products of the

TABLE 3

| Target | Primer | Sequence[a] | Product (base pairs) | Position[b] | Accession[c] |
| --- | --- | --- | --- | --- | --- |
| MOX12, CMY1, 8–11 | MOXMF | GCTGCTCAAGGAGCACAGGAT (SEQ ID NO:1) | 520 | 358–378 | D13304 |
|  | MOXMR | CACATTGACATAGGTGTGGTGC (SEQ ID NO:2) |  | 877–856 |  |
| LAT1–4, CMY2–7, BIL-1 | CITMF | TGGCCAGAACTGACAGGCAAA (SEQ ID NO:3) | 462 | 478–498 | X78117 |
|  | CITMR | TTTCTCCTGAACGTGGCTGGC (SEQ ID NO:4) |  | 939–919 |  |
| DHA1–2 | DHAMF | AACTTTCACAGGTGTGCTGGGT (SEQ ID NO:5) | 405 | 1244–1265 | Y16410 |
|  | DHAMR | CCGTACGCATACTGGCTTTGC (SEQ ID NO:6) |  | 1648–1628 |  |
| ACC-1 | ACCMF | AACAGCCTCAGCAGCCGGTTA (SEQ ID NO:7) | 346 | 861–881 | AJ133121 |
|  | ACCMR | TTCGCCGCAATCATCCCTAGC (SEQ ID NO:8) |  | 1206–1186 |  |
| MW-1, ACT-1 | EBCMF | TCGGTAAAGCCGATGTTGCGG (SEQ ID NO:9) | 302 | 1115–1135 | M37839 |
|  | EBCMR | CTTCCACTGCGGCTGCCAGTT (SEQ ID NO:10) |  | 1416–1396 |  |
| FOX1–5b (FOX 6, see GenBank accession number AY034848) | FOXMF | AACATGGGGTATCAGGGAGATG (SEQ ID NO:11) | 190 | 1475–1496 | X77455 |
|  | FOXMR | CAAAGCGCGTAACCGGATTGG (SEQ ID NO:12) |  | 1664–1644 |  |

[a]All primers are written 5' to 3' as synthesized.
[b]Nucleotide position of the primer in the sequence referred.
[c]GenBank accession number for the sequence used for primer design.

Individual primers were evaluated, using template DNA from the same representative members listed above, to assure that one primer set amplified only one amplicon. Amplification was only observed when each set of family-specific primers was used with template DNA from that particular ampC family. Using these parameters, only one amplicon of the predicted size was observed for each template, primer pair tested.

Plasmid-mediated ampC harboring control strains analysis. Sequences of ampC genes from the same family show slight variations, resulting in the individual family member. For example sequences of members of the proposed *Citrobacter*-origin family have a group homology of 98.6% (FIG.

expected size for Enterobacter-origin ampC genes were obtained when DNA from *E. cloacae* were used as template; this represents the EBC-product of 302 base pairs (Table 3), but no other set of ampC primers cross-reacted with this chromosomal DNA. In addition, products of the expected sizes for *Citrobacter-, Morganella-* and *Hafnia-*origin ampC genes was observed when DNA from *C. freundii, M. morganii,* and *H. alvei* were used as template. In addition, DNA template prepared from a *Citrobacter* spp. other than *C. freundii* did not result in an amplified product, indicating the specificity of this primer pair.

Figure 5A:
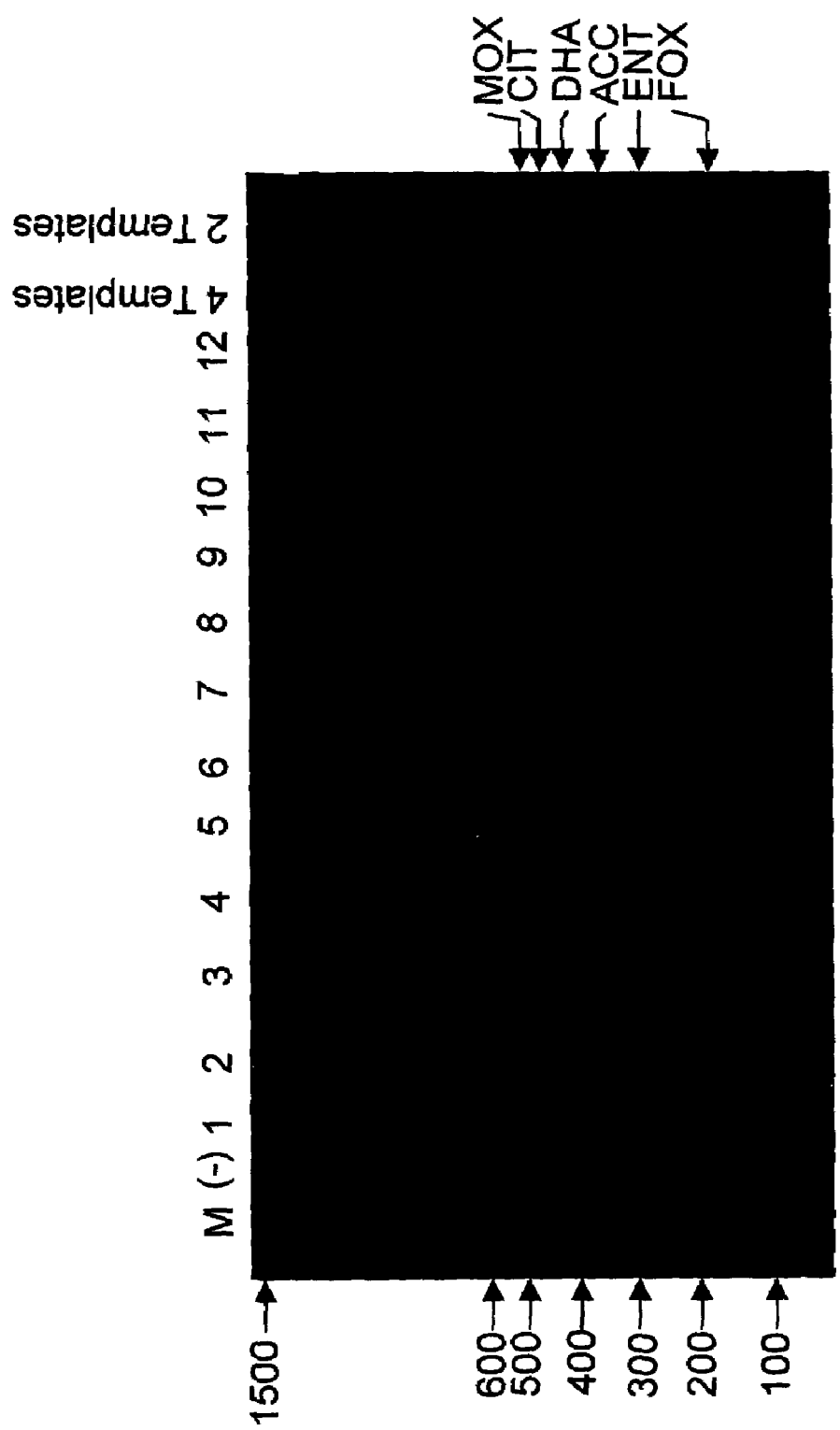
FIGS. 5A and 5B. Analysis of clinical isolates. Multiplex PCR products were separated in a 2% agarose gel. (M) 100 base pair DNA ladder (Life Technologies, Rockville, Md.); (−) negative water control; 4 templates (MOX-1, LAT-1, DHA-1, and ACC); 2 templates (FOX-1 and ACT-1); (C.o. (−)) carry over negative control.
Figure 5B:
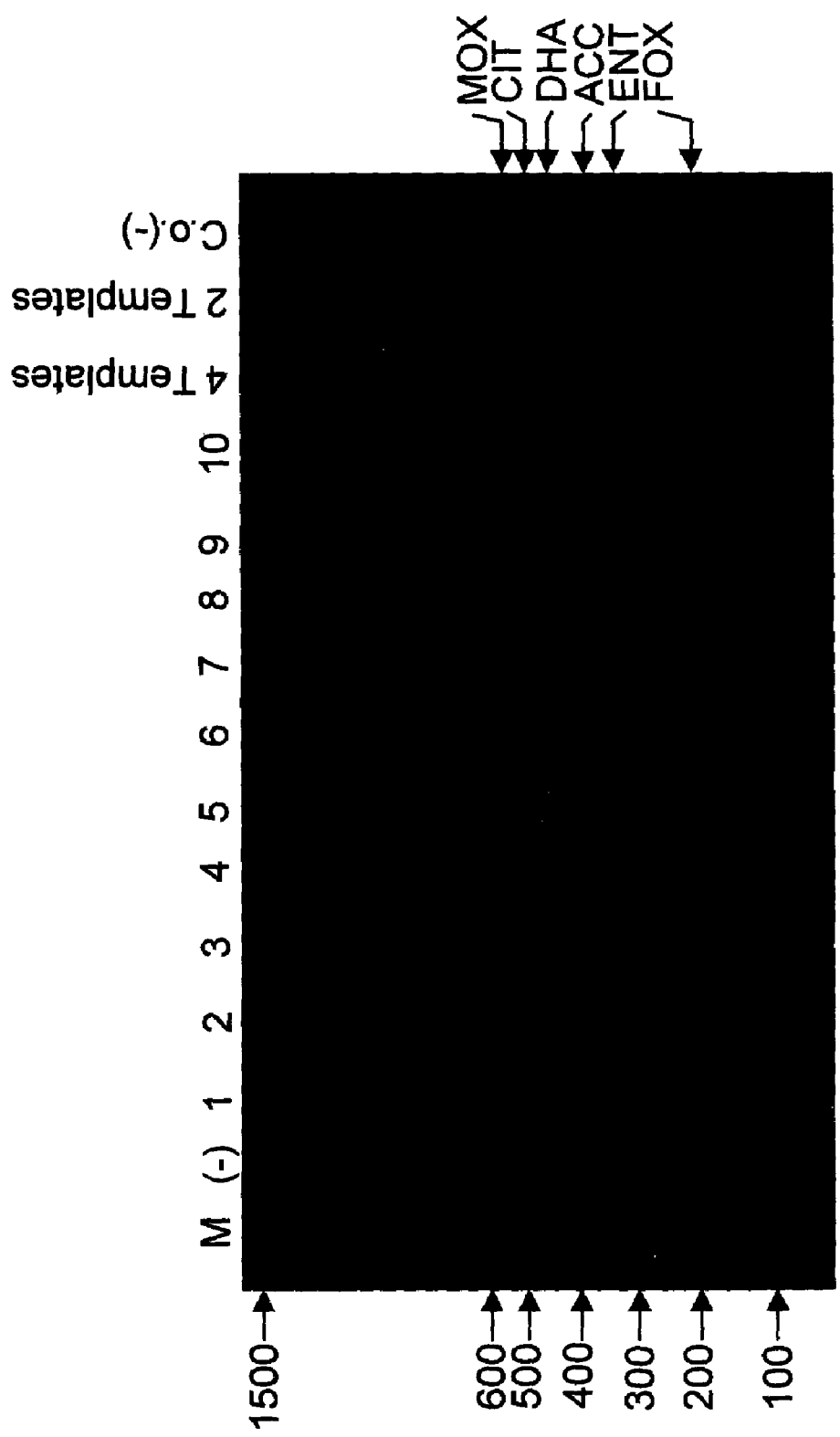

Analysis of clinical isolates. The data presented in FIGS. 2–4 indicate the specificity of the ampC multiplex PCR using highly characterized (both phenotypically and molecularly) strains. Twenty two clinical isolates were tested in order to substantiate that ampC multiplex PCR would be able to identify family-specific ampC genes also in isolates not previously characterized molecularly. Based on phenotypic characterization, these isolates were predicted to express an AmpC beta-lactamase. DNA from these isolates served as template in an ampC multiplex PCR assay (FIGS. 5A and 5B). Two PCR reactions using 2 templates (ACT-1 and FOX-1) or 4 templates (MOX-1, LAT-1, DHA-1 and ACC) were performed and separated in the same gel as markers for individual unknown reactions. PCR analysis indicated no amplification from DNA template of 12 isolates (FIG. 5A, lanes 1, 2, 3, 4, 6, 7, 8, 11 and 12; FIG. 5B, lanes 1, 2 and 11). A single product was amplified for II isolates. Five isolates resulted in an amplicon of approximately 200 base pairs (FOX-like) (FIG. 5A, lanes 5 and 9; FIG. 5B, lanes 3, 4 and 8), 2 isolates resulted in an amplicon of about 300 base pairs (*Enterobacter*-like) (FIG. 5B, lanes 7 and 9), one isolate resulted in an amplicon of about 400 base pairs (DHA-like) (FIG. 5B, lane 6), and 3 isolates generated an amplicon with a size of about 460 base pairs (*Citrobacter*-like) (FIG. 5A, lane 10; FIG. 5B, lanes 5 and 10). Template combinations of 2 or 4 templates were used as markers at the right of both gels in FIG. 5. Substantiation that the unknown isolates with specific amplified product were as predicted, one isolate was used for sequence analysis. The CIT-like result of ampC multiplex PCR (FIG. 5A, lane 10) was confirmed by the sequencing analysis, which showed a 100% identity between the base pairs of the PCR product sequenced and the gene $bla_{CMY-2}$.

WAVE analysis. Specificity and sensitivity are criteria used to evaluate diagnostic techniques used for identification. In clinical laboratories speed is also an important parameter. The time required to prepare template DNA and perform multiplex PCR was a total of about 1.5 hours. However, visualization of the PCR products by gel electrophoresis requires approximately four hours for high resolution of bands in 2% agarose, staining, destaining and finally interpretation of data. In order to reduce the total required time without loosing specificity and sensitivity, an HPLC-based nucleic acid analyzing technology known as WAVE was used.

Figure 2:
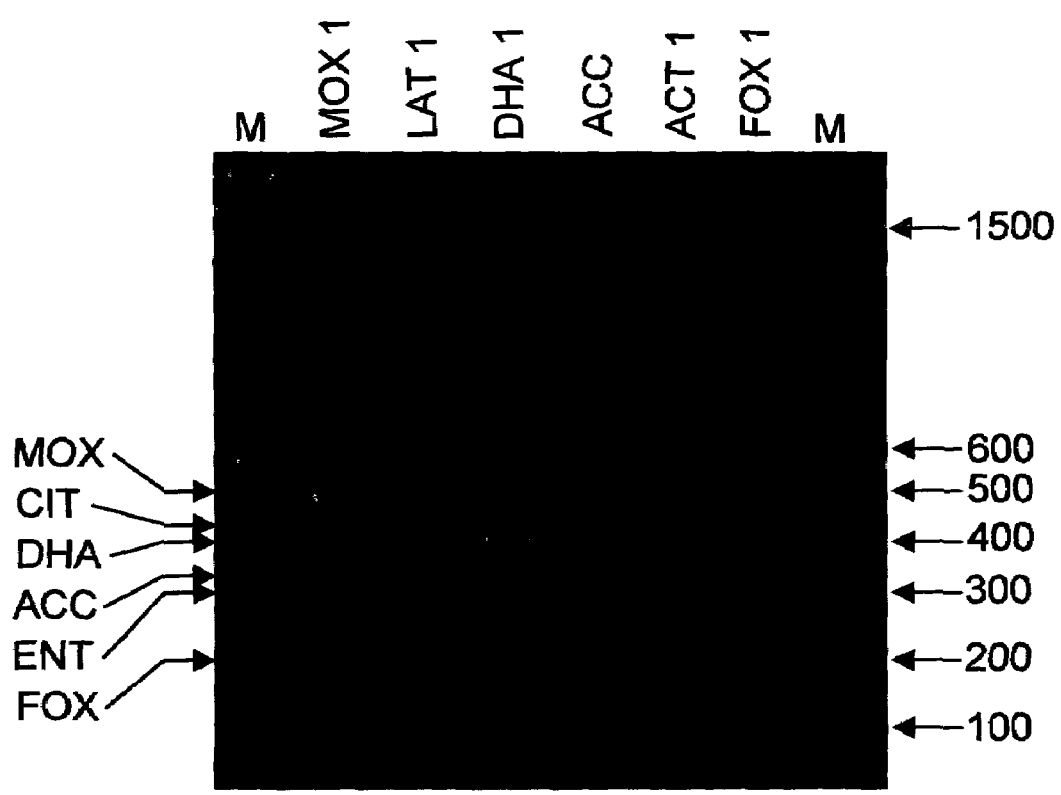
FIG. 2. Initial analysis of ampC multiplex polymerase chain reaction (PCR). Multiplex PCR products were separated in a 2% agarose gel. Lanes are labeled with the ampC gene used as template DNA; ACC represents the chromosomal ampC gene from *Hafnia alvei*; (M) 100 base pair (bp) DNA ladder (Life Technologies, Rockville, Md.). The amplified product from each PCR reaction is indicated on the left, the size of the marker in base pairs is shown on the right.

A comparison of gel electrophoresis and WAVE technology was performed using ampC multiplex PCR products from a representative member of each gene family (FIG. 2). Amplified products visualized by gel electrophoresis in FIG. 2. MOX (520 base pairs), CIT (462 base pairs), DHA (405 base pairs), ACC (346 base pairs), EBC (302 base pairs) and FOX (190 base pairs) correlate with the peaks observed in FIG. 6A, with retention times of 6.07 minutes, 5.78 minutes, 5.19 minutes, 4.76 minutes, 4.39 minutes, and 3.41 minutes, respectively. The initial peak at 0.5 minute and the final peak at 10 minutes in FIG. 6A correspond to injection and washing peaks, respectively.

Figure 6B:
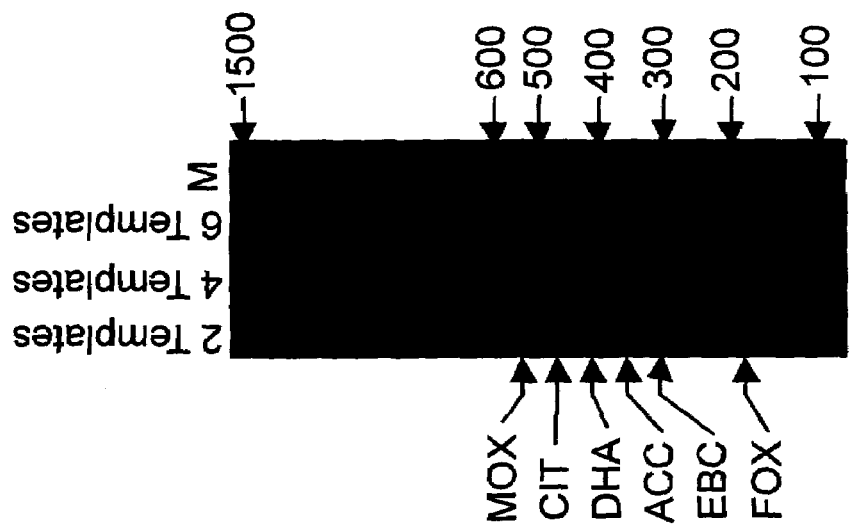
FIGS. 6A and 6B. WAVE analysis.
Figure 6A:
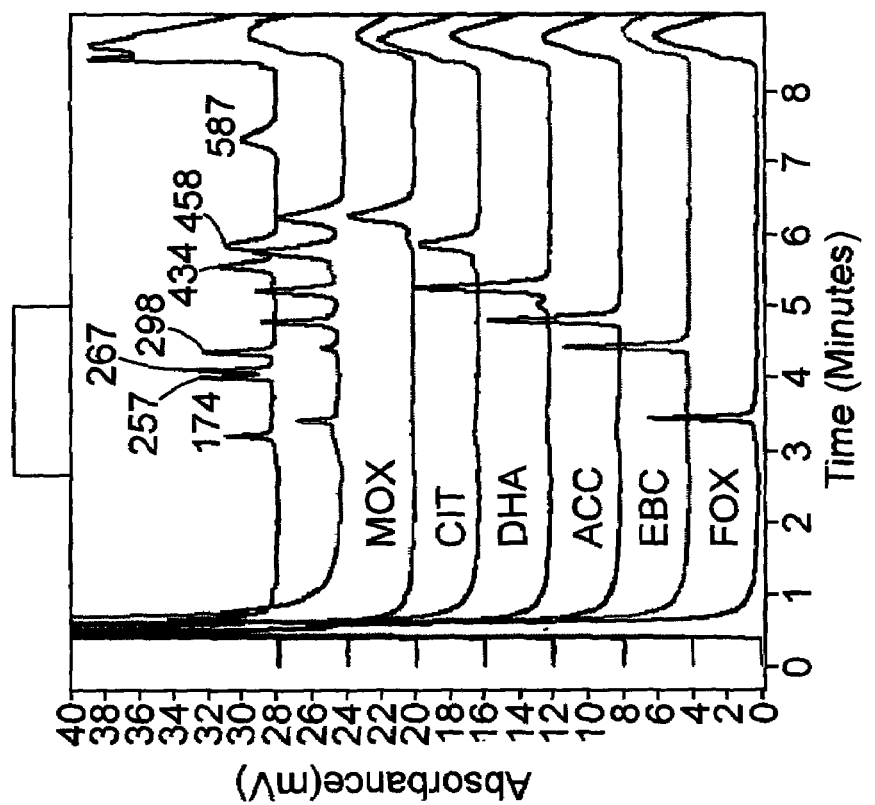

Multiple templates of 2 (FOX and EBC), 4 (MOX, CIT, DHA and ACC), or 6 (a combination of the 2 and 4 templates) were mixed and then amplified using ampC multiplex PCR. Amplification of two and four templates resulted in amplicons of the expected sizes and was visualized by agarose gel electrophoresis and ethidium bromide staining, as shown in FIG. 6B. However, visualization of six amplified products was difficult, resulting in only four amplified products being readily visible. A sample from the same PCR reaction which generated the six amplification products analyzed by gel electrophoresis was analyzed by the WAVE. All six products were observed by well-defined peaks (FIG. 6A). Each peak had a retention time equivalent to the observed retention times for single-template amplification, and was consistent with the expected size when compared to the size standard.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

SEQUENCE LISTING FREE TEXT

SEQ ID NO:1–12 Primer

What is claimed is:

1. A method for identifying the presence or absence of an AmpC beta-lactamase gene in a clinical sample, wherein the nucleic acid of an AmpC beta-lactamase gene, if present, are of a different origin relative to a bacteria's chromosomal ampC beta-lactamase nucleic acid, the method comprising:
providing a clinical sample;
contacting the clinical sample with at least two pairs of oligonucleotide primers specific for nucleic acid of an AmpC beta-lactamase gene, wherein one primer of each pair is complementary to at least a portion of an ampC beta-lactamase nucleic acid in the sense strand and the other primer of each pair is complementary to at least a portion of an ampC beta-lactamase nucleic acid in the antisense strand;
annealing the primers to the ampC beta-lactamase nucleic acid, if present;
simultaneously extending the annealed primers from a 3' terminus of each primer to synthesize an extension product that is complementary to the nucleic acid strands annealed to each primer wherein each extension product after separation from the ampC beta-lactamase nucleic acid, if present, serves as a template for the synthesis of an extension product for the other primer of each pair; and
analyzing the sample for the presence or absence of amplified products, wherein the presence of amplified products of a size characteristic of an ampC beta-lactamase nucleic acid indicates the presence of an AmpC beta-lactamase gene in the clinical sample.

2. The method of claim 1 wherein the ampC beta-lactamase nucleic acid comprise transferable ampC beta-lactamase nucleic acid.

3. The method of claim 2 wherein the transferable ampC beta-lactamase nucleic acid comprise plasmid-mediated ampC beta-lactamase nucleic acid.

4. A method for identifying the presence or absence of an AmpC beta-lactamase gene in a clinical sample, wherein the nucleic acid of an AmpC beta-lactamase gene, if present, are of a different origin relative to a bacteria's chromosomal ampC beta-lactamase nucleic acid, the method comprising:
providing a clinical sample;
contacting the clinical sample with at least two pairs of oligonucleotide primers specific for nucleic acid of an AmpC beta-lactamase gene, wherein one primer of each pair is complementary to at least a portion of an ampC beta-lactamase nucleic acid in the sense strand and the other primer of each pair is complementary to at least a portion of an ampC beta-lactamase nucleic acid in the antisense strand;

annealing the primers to the ampC beta-lactamase nucleic acid, if present;

simultaneously extending the annealed primers from a 3' terminus of each primer to synthesize an extension product that is complementary to the nucleic acid strands annealed to each primer wherein each extension product after separation from the ampC beta-lactamase nucleic acid, if present, serves as a template for the synthesis of an extension product for the other primer of each pair; and analyzing the sample for the presence or absence of amplified products, wherein the presence of amplified products of a size characteristic of an ampC beta-lactamase nucleic acid indicates the presence of an AmpC beta-lactamase gene in the clinical sample, wherein the primers are selected from the group consisting of MOXMF (SEQ ID NO:1), MOXMR (SEQ ID NO:2), CITMF (SEQ ID NO:3), CITMR (SEQ ID NO:4), DHAMF (SEQ ID NO:5), DHAMR (SEQ ID NO:6), ACCMF (SEQ ID NO:7), ACCMR (SEQ ID NO:8), EBCMF (SEQ ID NO:9), EBCMR (SEQ ID NO:10), FOXMF (SEQ ID NO:11), FOXMR (SEQ ID NO:12), and full-length complements thereof.

5. The method of claim 1 wherein the primers are specific for nucleic acid characteristic of an AmpC beta-lactamase gene designated as MOX1-2 and CMY1, 8-11, and their chromosomal origin.

6. The method of claim 5 wherein the primers are selected from the group consisting of:

5' - GCTGCTCAAGGAGCACAGGAT - 3'  (SEQ ID NO:1);

5' - CACATTGACATAGGTGTGGTGC - 3' (SEQ ID NO:2);
and full-length complements thereof.

7. The method of claim 1 wherein the primers are specific for nucleic acid characteristic of an AmpC beta-lactamase gene designated as LAT1-4, CMY2-7, and BIL-1, and their chromosomal origin.

8. The method of claim 7 wherein the primers are selected from the group consisting of:

5' - TGGCCAGAACTGACAGGCAAA - 3' (SEQ ID NO:3);

5' - TTTCTCCTGAACGTGGCTGGC - 3' (SEQ ID NO:4);
and full-length complements thereof.

9. The method of claim 1 wherein the primers are specific for nucleic acid characteristic of an AmpC beta-lactamase gene designated as DHA1-2, and their chromosomal origin.

10. The method of claim 9 wherein the primers are selected from the group consisting of:

5' - AACTTTCACAGGTGTGCTGGGT - 3' (SEQ ID NO:5);

5' - CCGTACGCATACTGGCTTTGC - 3'  (SEQ ID NO:6);
and full-length complements thereof.

11. The method of claim 1 wherein the primers are specific for nucleic acid characteristic of an AmpC beta-lactamase gene designated as ACC-1, and their chromosomal origin.

12. The method of claim 11 wherein the primers are selected from the group consisting of:

5' - AACAGCCTCAGCAGCCGGTTA - 3' (SEQ ID NO:7);

5' - TTCGCCGCAATCATCCCTAGC - 3' (SEQ ID NO:8);
and full-length complements thereof.

13. The method of claim 1 wherein the primers are specific for nucleic acid characteristic of an AmpC beta-lactamase gene designated as MIR-1 and ACT-1, and their chromosomal origin.

14. The method of claim 13 wherein the primers are selected from the group consisting of:

5' - TCGGTAAAGCCGATGTTGCGG - 3' (SEQ ID NO:9);

5' - CTTCCACTGCGGCTGCCAGTT - 3' (SEQ ID NO:10);
and full-length complements thereof.

15. The method of claim 1 wherein the primers are specific for nucleic acid characteristic of an AmpC beta-lactamase gene designated as FOX1-5b, and their chromosomal origin.

16. The method of claim 15 wherein the primers are selected from the group consisting of:

5' - AACATGGGGTATCAGGGAGATG - 3'  (SEQ ID NO:11);

5' -CAAAGCGCGTAACCGGATTGG - 3'    (SEQ ID NO:12);
and full-length complements thereof.

17. The method of claim 1 wherein contacting the clinical sample with the at least two pairs of oligonucleotide primers comprises contacting the clinical sample with 2–6 pairs of primers.

18. The method of claim 17 wherein contacting the clinical sample with the at least two pairs of oligonucleotide primers comprises contacting the clinical sample with 4–6 pairs of primers.

19. The method of claim 1 wherein analyzing the sample comprises separating amplified products from the sample and analyzing the separated amplified products for a size characteristic of a particular type of AmpC beta-lactamase gene by performing WAVE analysis.

20. The method of claim 1 wherein analyzing the sample comprises separating amplified products from the sample and analyzing the separated amplified products for a size characteristic of a particular type of AmpC beta-lactamase gene by performing electrophoresis.

21. A method for identifying different types of ampC beta-lactamase nucleic acid in a clinical sample, wherein the ampC beta-lactamase nucleic acid are of a different origin relative to a bacteria's chromosomal ampC beta-lactamase nucleic acid, the method comprising:

providing a clinical sample;

contacting the clinical sample with at least two pairs of oligonucleotide primers specific for nucleic acid of a particular type of AmpC beta-lactamase gene, wherein one primer of each pair is complementary to at least a portion of the ampC beta-lactamase nucleic acid in the sense strand and the other primer of each pair is complementary to at least a portion of the ampC beta-lactamase nucleic acid in the antisense strand;

annealing the primers to the ampC beta-lactamase nucleic acid;

simultaneously extending the annealed primers from a 3' terminus of each primer to synthesize an extension product that is complementary to the nucleic acid strands annealed to each primer wherein each extension product after separation from the ampC beta-lactamase nucleic acid serves as a template for the synthesis of an extension product for the other primer of each pair;
separating the amplified products; and
analyzing the separated amplified products for a size characteristic of the particular type of AmpC beta-lactamase gene.

22. A method for identifying the presence of plasmid-mediated ampC beta-lactamase nucleic acid in a clinical sample, wherein the plasmid-mediated ampC beta-lactamase nucleic acid are of a different origin relative to a bacteria's chromosomal ampC beta-lactamase nucleic acid, the method comprising:
providing a clinical sample;
contacting the clinical sample with 2–6 pairs of oligonucleotide primers specific for nucleic acid of plasmid-mediated AmpC beta-lactamase gene, wherein one primer of each pair is complementary to at least a portion of a plasmid-mediated ampC beta-lactamase nucleic acid in the sense strand and the other primer of each pair is complementary to at least a portion of a plasmid-mediated ampC beta-lactamase nucleic acid in the antisense strand;
annealing the primers to the plasmid-mediated ampC beta-lactamase nucleic acid, if present;
simultaneously extending the annealed primers from a 3' terminus of each primer to synthesize an extension product that is complementary to the nucleic acid strands annealed to each primer wherein each extension product after separation from the plasmid-mediated ampC beta-lactamase nucleic acid serves as a template for the synthesis of an extension product for the other primer of each pair; and
analyzing the sample for amplified products characteristic of a plasmid-mediated AmpC beta-lactamase gene.

23. The method of claim 22 wherein analyzing the sample comprises separating the amplified products and analyzing the separated amplified products for a size characteristic of an AmpC beta-lactamase gene.

24. The method of claim 22 wherein the at least two pairs of oligonucleotide primers are selected from the group consisting of:

5'-GCTGCTCAAGGAGCACAGGAT-3';    (SEQ ID NO:1)

5'-CACATTGACATAGGTGTGGTGC-3';    (SEQ ID NO:2)

5'-TGGCCAGAACTGACAGGCAAA-3';    (SEQ ID NO:3)

5'-TTTCTCCTGAACGTGGCTGGC-3';    (SEQ ID NO:4)

5'-AACTTTCACAGGTGTGCTGGGT-3';    (SEQ ID NO:5)

5'-CCGTACGCATACTGGCTTTGC-3';    (SEQ ID NO:6)

5'-AACAGCCTCAGCAGCCGGTTA-3';    (SEQ ID NO:7)

5'-TTCGCCGCAATCATCCCTAGC-3';    (SEQ ID NO:8)

5'-TCGGTAAAGCCGATGTTGCGG-3';    (SEQ ID NO:9)

5'-CTTCCACTGCGGCTGCCAGTT-3';    (SEQ ID NO:10)

5'-AACATGGGGTATCAGGGAGATG-3';    (SEQ ID NO:11)

5'-CAAAGCGCGTAACCGGATTGG-3';    (SEQ ID NO:12)

and complements thereof.

25. A method for identifying different types of ampC beta-lactamase nucleic acid in a clinical sample, wherein the ampC beta-lactamase nucleic acid are of a different origin relative to a bacteria's chromosomal ampC beta-lactamase nucleic acid, the method comprising:
providing a clinical sample comprising at least two different types of ampC beta lactamase nucleic acid;
contacting the clinical sample with at least two pairs of oligonucleotide primers specific for nucleic acid of a particular type of AmpC beta-lactamase gene, wherein one primer of each pair is complementary to at least a portion of the ampC beta-lactamase nucleic acid in the sense strand and the other primer of each pair is complementary to at least a portion of the ampC beta-lactamase nucleic acid in the antisense strand;
annealing the primers to the ampC beta-lactamase nucleic acid;
simultaneously extending the annealed primers from a 3' terminus of each primer to synthesize an extension product that is complementary to the nucleic acid strands annealed to each primer wherein each extension product after separation from the ampC beta-lactamase nucleic acid serves as a template for the synthesis of an extension product for the other primer of each pair;
separating the amplified products; and
analyzing the separated amplified products for a size characteristic of the particular type of AmpC beta-lactamase gene.

* * * * *

```
                           SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gctgctcaag gagcacagga t                                                 21

<210> SEQ ID NO 2
<211> LENGTH: 22
<212> TYPE: DNA
<213> ORGANISM: Artificial Sequence
<220> FEATURE:
<223> OTHER INFORMATION: Primer
```

```
<400> SEQUENCE: 2
cacattgaca taggtgtggt gc                                              22

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
tggccagaac tgacaggcaa a                                               21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
tttctcctga acgtggctgg c                                               21

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
aactttcaca ggtgtgctgg gt                                              22

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
ccgtacgcat actggctttg c                                               21

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
aacagcctca gcagccggtt a                                               21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ttcgccgcaa tcatccctag c                                               21
```

-continued

```
<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
tcggtaaagc cgatgttgcg g                                          21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
cttccactgc ggctgccagt t                                          21

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
aacatggggt atcaggaga tg                                          22

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
caaagcgcgt aaccggattg g                                          21
```